(12) United States Patent
Prechtl et al.

(10) Patent No.: US 6,485,527 B1
(45) Date of Patent: Nov. 26, 2002

(54) USE OF REACTIVE DYES FOR DYEING HAIR

(75) Inventors: Frank Prechtl, Mannheim; Manfred Patsch, Wachenheim; Peter Hössel, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/462,679

(22) PCT Filed: Jul. 3, 1998

(86) PCT No.: PCT/EP98/04104

§ 371 (c)(1),
(2), (4) Date: Jan. 11, 2000

(87) PCT Pub. No.: WO99/05222

PCT Pub. Date: Feb. 4, 1999

(30) Foreign Application Priority Data

Jul. 21, 1997 (DE) .......................... 197 31 166

(51) Int. Cl.⁷ ................................. A61K 7/13
(52) U.S. Cl. ................. 8/405; 8/406; 8/411; 8/412; 424/401; 424/407; 424/60; 424/70.6
(58) Field of Search ............... 8/405, 406, 411, 8/412; 424/401, 407, 60, 70.6

(56) References Cited

U.S. PATENT DOCUMENTS 5,250,670 A * 10/1993 Schlafer et al. ............. 534/642
5,548,071 A * 8/1996 Deitz et al. .................. 534/612
5,976,195 A * 11/1999 de al Mettrie et al. ......... 8/411

* cited by examiner

Primary Examiner—Yogendra N. Gupta
Assistant Examiner—Eisa Elhilo
(74) Attorney, Agent, or Firm—Oblon, Spivak, McClelland, Maier & Neustadt, P.C.

(57) ABSTRACT

Reactive dyes of the formula I

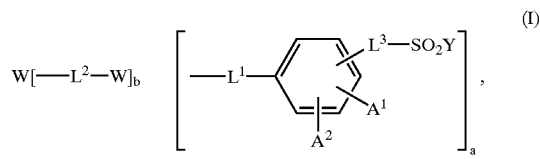

where
a is 1 or 2,
b is 0 or 1,
Y is vinyl or a radical of the formula $C_2H_4Q$, where Q is an alkali-detachable group,
$L^3$ is a direct bond or a bridge member of the formula CO—NH—$M^1$, where $M^1$ is $C_2$–$C_6$-alkylene with or without interruption by 1 or 2 unadjacent oxygen atoms, imino or $C_1$–$C_4$-alkylimino groups,
$A^1$ is hydroxysulfonyl or a radical of the formula $SO_2Y$,
$A^2$ is hydrogen, hydroxysulfonyl, methoxy, chlorine, bromine or carboxyl,
W is either in case 1) the radical of a coupling component, of a monoazo dye or additionally, when b=0, of a disazo dye, which may each bear further fiber-reactive groups, or
in case 2) the radical of a chromophore which optionally has further reactive groups,
$L^1$ and $L^2$ are each a bridge member,
are useful for hair dyeing and for use in cosmetic preparations for dyeing hair.

25 Claims, No Drawings

USE OF REACTIVE DYES FOR DYEING HAIR

The present invention relates to the use of reactive dyes of the formula I $$W[\text{—}L^2\text{—}W]_b \quad \left[\text{—}L^1\text{—}\underset{A^2}{\overset{L^3\text{—}SO_2Y}{\bigcirc}}\text{—}A^1\right]_a \quad (I)$$

where a is 1 or 2, b is 0 or 1,

Y is vinyl or a radical of the formula $C_2H_4Q$, where Q is an alkali-detachable group, $L^3$ is a direct bond or a bridge member of the formula CO—NH—$M^1$, where $M^1$ is $C_2$–$C_6$-alkylene with or without interruption by 1 or 2 unadjacent oxygen atoms, imino or $C_1$–$C_4$-alkylimino groups, $A^1$ is hydroxysulfonyl or a radical of the formula $SO_2Y$, $A^2$ is hydrogen, hydroxysulfonyl, methoxy, chlorine, bromine or carboxyl, W is either in case 1) the radical of a coupling component, of a monoazo dye or additionally, when b=0, of a disazo dye, which may each bear further fiber-reactive groups, or in case 2) the radical of a chromophore which optionally has further fiber-reactive groups and is derived from an optionally metallized mono- or disazo dye, from a triphendioxazine, from an anthraquinone, from a metallized formazan or from a metallized phthalocyanine, $L^1$ is either in case 1) an azo bridge or in case 2) a bridge member of the formula $O_2S$—$NZ^1$, OC—$NZ^1$, $Z^1N$—$SO_2$, $Z^1N$—CO, $Z^1N$—CO—$NZ^2$, $NZ^1$ or

[triazine structure with $Z^1$, $Z^2$, $M^2$, X substituents]

where $M^2$ is a direct bond or methylene, $Z^1$ and $Z^2$ are each independently of the other hydrogen, $C_1$–$C_6$-alkyl or phenyl and X is fluorine, chlorine or bromine, amino, $C_1$–$C_6$-alkylamino with or without interruption by 1 or 2 unadjacent oxygen atoms, imino or $C_1$–$C_4$-alkylimino groups and with or without hydroxyl substitution, N-pyrrolidinyl, N-piperidinyl, N-morpholinyl, N-piperazinyl or N—($C_1$–$C_4$)-alkylpiperazinyl, or $NZ^1$ or $Nz^2$ each also represent 1,4-piperazinediyl, $L^2$ is a radical of the formula

[bis-triazine structures with $Z^3$, $Z^4$, $Z^5$, $Z^6$, $L^4$, X substituents]

where $Z^3$, $Z^4$, $Z^5$ and $Z^6$ are each independently of the others hydrogen, $C_1$–$C_6$-alkyl or phenyl, $L^4$ is $C_2$–$C_8$-alkylene or unsubstituted or $C_1$–$C_4$-alkyl-, $C_1$–$C_4$-alkoxy- or hydroxysulfonyl-substituted phenylene, and X is in each case as defined above, for dyeing hair, to a method for hair dyeing and to cosmetic preparations for dyeing hair.

The use of reactive dyes falling within the general formula I for dyeing nitrogenous fibers such as wool is known, for example, from U.S. Pat. No. 4,066,638, EP-A-107 614, EP-A-559 617, DE-A-3,441,273 and DE-A-2,154,942. Depending on the dyeing process, dyeing prescriptions for cotton and wool involve a pH of 10–12, temperatures within the range from 60 to 80° C. and treatment times around the 10 hour mark.

U.S. Pat. No. 4,102,641 discloses the use of halotriazinyl reactive dyes for dyeing hair.

JP-A-75 025 529 describes dye formulations for use as hair dyes. The reactive dyes used therein are based on p-sulfatoethylsulfonylaniline as diazo component and fiber-reactive radical. Therefore dyeing with these dyes requires relatively long treatment times.

It is an object of the present invention to provide dyes for dyeing hair under benign dyeing conditions, such as mild pH, short treatment times and low temperatures.

We have found that this object is achieved by the use of reactive dyes of the general formula I for dyeing human hair.

The reactive dyes of the formula I are each indicated in the form of the free acid. It will be appreciated that the use of their physiologically acceptable salts is likewise encompassed by the present invention.

Suitable cations are derived from metal or ammonium ions. Metal ions are especially lithium, sodium or potassium ions. Ammonium ions for the purposes of the present invention are substituted or unsubstituted ammonium cations. Examples of substituted ammonium cations are monoalkyl-, dialkyl-, trialkyl-, tetraalkyl- or benzyltrialkyl-ammonium cations or those cations derived from nitrogenous five- or six-membered saturated heterocycles, such as pyrrolidinium, piperidinium, morpholinium, piperazinium or N-alkylpiperazinium cations or their N-monoalkyl- or N,N-dialkyl-substituted products. Alkyl is generally straight-chain or branched $C_1$–$C_{20}$-alkyl, which may be substituted by 1 or 2 hydroxyl groups and/or interrupted by from 1 to 4 oxygen atoms in ether function.

In general, all alkyl and alkylene groups mentioned above and appearing in the formulae which follow may be straight-chain or branched.

Substituted alkyl radicals preferably contain, unless otherwise stated, 1, 2 or 3 substituents, especially 1 or 2 substituents, in any desired position.

$Z^1$, $Z^2$, $Z^3$, $Z^4$, $Z^5$ and $Z^6$ are each for example methyl, ethyl, propyl, isopropyl, butyl, isobutyl, sec-butyl, tert-butyl, pentyl, isopentyl, neopentyl, tert-pentyl, hexyl or 2-methylpentyl.

$M^1$ and $L^4$ are each for example $(CH_2)_2$, $(CH_2)_3$, $(CH_2)_4$, $CH(CH_3)CH_2$, $CH(CH_3)CH(CH_3)$, $(CH_2)_5$, $(CH_2)_6$.

$M^1$ may also be $(CH_2)_2O(CH_2)_2$, $(CH_2)_3O(CH_2)_2$, $(CH_2)_2O(CH_2)_2O(CH_2)_2$, $(CH_2)_2NH(CH_2)_2$, $(CH_2)_3NH(CH_2)_2$, $(CH_2)_2NH(CH_2)_2NH(CH_2)_2$,

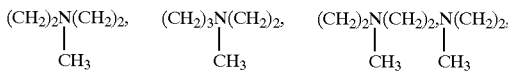

$L^4$ may also be for example $(CH_2)_7$, $(CH_2)_8$, 1,2-, 1,3- or 1,4-phenylene, which may be mono- or disubstituted by methyl, methoxy or hydroxysulfonyl.

X is methylamino, ethylamino, propylamino, isopropylamino, butylamino, isobutylamino, tert-butylamino, pentylamino, hexylamino, hydroxymethylamino, 2-hydroxyethylamino, 2- or 3-hydroxypropylamino, 2- or 4-hydroxybutylamino, methoxymethylamino, 2-methoxyethylamino, 2- or 3-methoxypropylamino, 2- or 4-methoxybutylamino, ethoxymethylamino, ethoxyethylamino, ethoxypropylamino, ethoxybutylamino, propoxyethylamino or propoxypropylamino.

Q is an alkali-detachable group. Such groups include for example chlorine, bromine, $C_1$–$C_4$-alkylsulfonyl, phenylsulfonyl, $OSO_3H$, $SSO_3H$, $OP(O)(OH)_2$, $C_1$–$C_4$-alkylsulfonyloxy, phenylsulfonyloxy, $C_1$–$C_4$-alkanoyloxy, $C_1$–$C_4$-dialkylamino or a radical of the formula

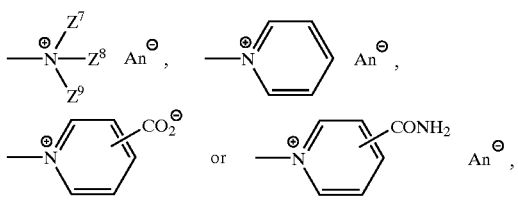

where $Z^7$, $Z^8$ and $Z^9$ are identical or different and each is independently of the others $C_1$–$C_4$-alkyl or benzyl and $An^{\ominus}$ is in each case one equivalent of an anion. Suitable anions include for example fluoride, chloride, bromide, iodide, mono-, di- or trichloroacetate, methanesulfonate, benzenesulfonate or 2- or 4-methylbenzenesulfonate.

When a is 2, the radicals

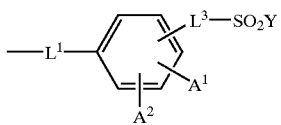

can be identical or different.

When b is 1, the radicals W can likewise be identical or different.

The fiber-reactive group of the formula II

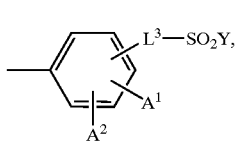
(II)

where $A^1$, $A^2$, $L^3$ and Y are each as defined above, will hereinafter be referred to as "E".

Preference for use in the dyeing of hair is given to reactive dyes of the formula I where $L^3$ is a direct bond.

Preference is further given to the use of reactive dyes of the formula I where $A^1$ is hydroxysulfonyl.

Preference is likewise given to the use of reactive dyes of the formula I where $L^3$ is a direct bond and $A^1$ is a radical of the formula $SO_2Y$.

Preference for the use in dyeing hair is also given to reactive dyes of the formula I where $A^2$ is hydrogen or especially hydroxysulfonyl.

Preference for use in the dyeing of hair is further given to reactive dyes of the formula I where $L^1$ is an azo bridge.

Preference is also given to the use of reactive dyes of the formula I where $L^1$ is a bridge member of the formula

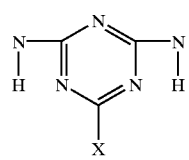

and X is as defined above.

Particular preference is given to the use of reactive dyes of the formula I where the hydroxysulfonyl radical is disposed ortho or para to $L^1$ and the fiber-reactive radical is disposed para or ortho to $L^1$ or para to the hydroxysulfonyl radical.

Reactive dyes of the formula I whose fiber-reactive radical conforms to the formula II a–g

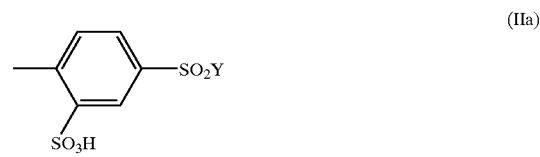
(IIa)

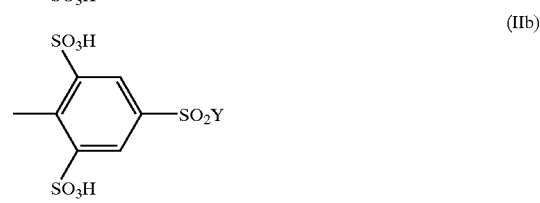
(IIb)

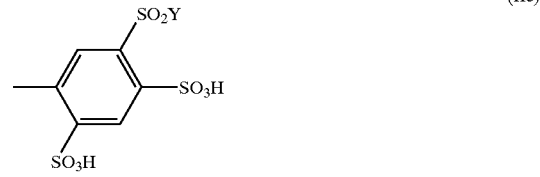
(IIc)

(IId)

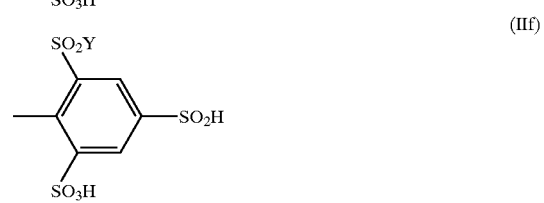
(IIf)

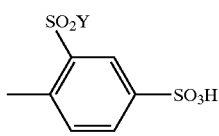

are very particularly preferred for dyeing hair.

Preference for use in the dying of hair is further given to reactive dyes of the formula I where Y is a radical of the formula —$C_2H_4SSO_3H$, —$C_2H_4Cl$, —$C_2H_4OCOCH_3$ and particularly —$C_2H_4OSO_3H$ or especially vinyl.

Preference is also given to the use of dyes of the formula I where the substituents are selected from a combination of the above-recited preferred substituents.

The $SO_2Y$ radicals are additively reacting fiber-reactive radicals, which are distinguished from the substitutively reacting fiber-reactive radicals.

Substitutive reaction of the fiber-reactive group with the relevant nucleophilic groups (HNuc-) in the substrates, for example with the amino groups of hair, means that the leaving groups or atoms (eg. fluorine or chlorine) in the fiber-reactive radical are substitutively replaced by the amino groups of the hair as per the following scheme:

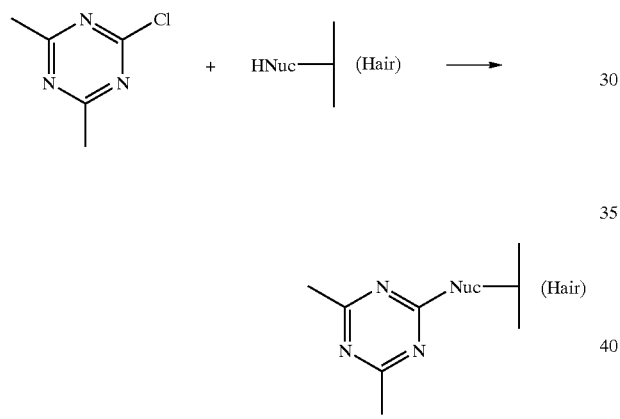

Additive reaction of the fiber-reactive group with the relevant groups in the substrates, for example with the amino groups of hair, means that the amino groups of the hair undergo an addition reaction with the fiber-reactive group as per the following scheme:

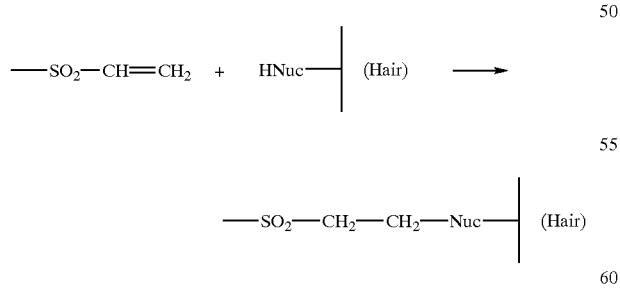

Examples of substitutively reacting fiber-reactive radicals are halogen-substituted radicals derived from 1,3,5-triazine, quinoxaline, phthalazine, pyrimidine, pyridazine or 2-alkylsulfonylbenzothiazole as heterocyclic parent species.

The following heterocyclic radicals are particularly suitable:

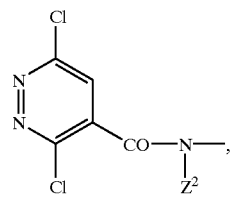

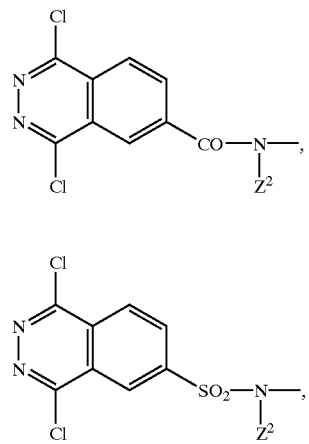

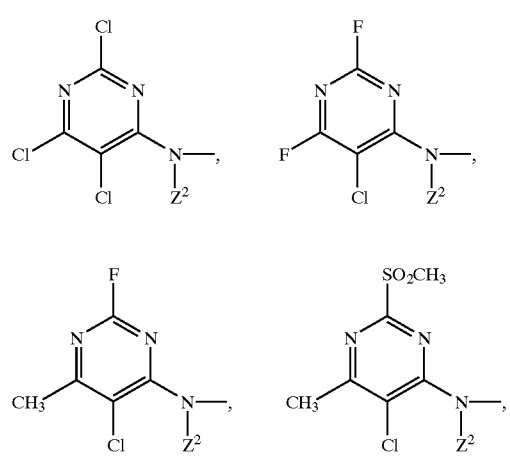

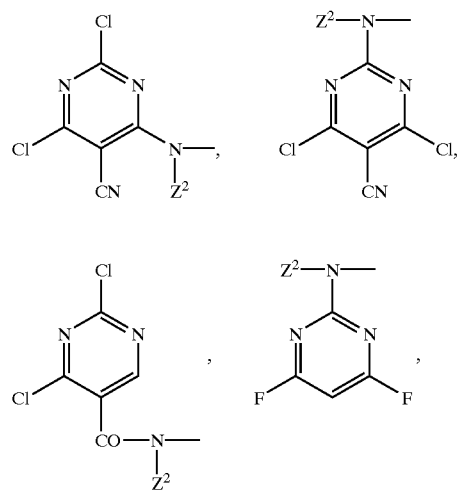

-continued

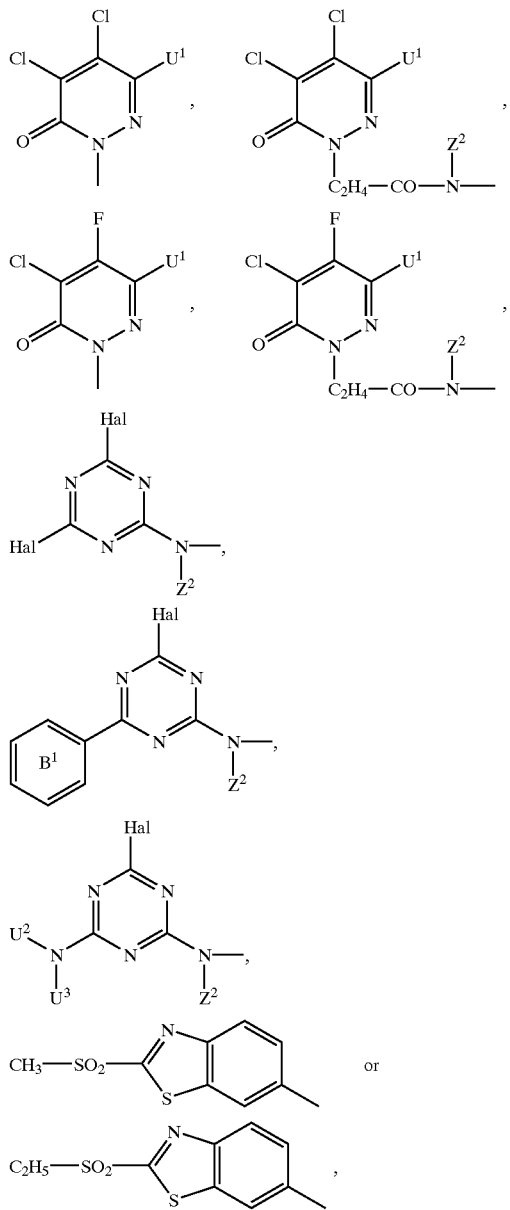

where $Z^2$ is as defined above,

Hal is fluorine, chlorine or bromine, $U^1$ is hydrogen or nitro, and $U^2$ and $U^3$ are independently hydrogen or $C_1$–$C_6$-alkyl with or without substitution by hydroxyl, halogen, cyano, hydroxysulfonyl or a radical of the formula —$SO_2$—Y, where Y is as defined above, and in each case with or without interruption by 1 or 2 oxygen atoms in ether function, imino or $C_1$–$C_4$-alkylimino groups, or $U^2$ and $U^3$ are together with the linking nitrogen atom pyrrolidinyl, piperidinyl, morpholinyl, piperazinyl or N—($C_1$–$C_4$-alkyl)piperazinyl, or $U^2$ can also be a radical of the formula

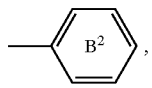

and the rings $B^1$ and $B^2$ may each be mono- or disubstituted by hydroxysulfonyl and/or benzofused, and the ring $B^2$ may independently be mono- or disubstituted by chlorine, nitro, $C_1$–$C_4$-alkyl, $C_1$–$C_4$-alkoxy, cyano, carboxyl, acetylamino, hydroxysulfonylmethyl or a radical of the formula $CH_2$—$SO_2$—Y, $SO_2$—Y, NH—CO—Y or $NU^2$—CO—$NU^2$—$L^5$—$SO_2$—Y, where Y and $U^2$ are each as defined above and $L^5$ is $C_2$–$C_6$-alkylene with or without substitution by hydroxyl, chlorine, cyano, carboxyl, $C_1$–$C_4$-alkoxycarbonyl, $C_1$–$C_4$-alkanoyloxy or sulfato and with or without interruption by 1 or 2 oxygen atoms in ether function or imino or $C_1$–$C_4$-alkylimino groups.

Examples of additively reacting fiber-reactive radicals are acryloyl, mono-, di- or trichloroacryloyl, mono-, di- or tribromoacryloyl, —CO—CCl=CH—COOH, —CO—CH=CCl—COOH, 2-chloropropionyl, 1,2-dichloropropionyl, 1,2-dibromopropionyl, 3-phenylsulfonylpropionyl, 3-methylsulfonylpropionyl, 2-sulfatoethylaminosulfonyl, 2-chloro-2,3,3-trifluorocyclobutylcarbonyl, 2,2,3,3-tetrafluorocyclobutylcarbonyl, 2,2,3,3-tetrafluorocyclobutylsulfonyl, 2-(2,2,3,3-tetrafluorocyclobutyl)acryloyl, 1- or 2-alkyl- or 1- or 2-arylsulfonylacryloyl, such as 1- or 2-methylsulfonylacryloyl, or a radical of the formula $SO_2$—Y, CONH—$L^6$—$SO_2$—Y or NHCONH—$L^6$—$SO_2$—Y, where Y is as defined above and $L^6$ is $C_1$–$C_4$-alkylene or phenylene.

W in the formula I is in case 1) for example the radical of a coupling component, of a monoazo dye or additionally, when b=0, of a disazo dye which optionally has additional fiber-reactive groups. In this case, the fiber-reactive group E is linked to the radical W via an azo bridge (—N=N—). If W is a monoazo dye, its coupling component will be linked to the fiber-reactive group E via an azo bridge. Correspondingly, if W is a disazo dye, coupling takes place onto its diazo component.

Reactive dyes of this class suitable for hair dyeing conform for example to the formula IIIa, IIIb, IIIc or IIId

| | |
|---|---|
| (E—N=N—)$_a$K | (IIIa) |
| E—N=N—K—N=N—D | (IIIb) |
| E—N=N—(K—N=N—D)—N=N—D | (IIIc) |
| (E—N=N—)$_2$(—K—N=N—D) | (IIId) | where K is the radical of a coupling component, D is the radical of a diazo component, a is 1 or 2 and E is as defined above. If, in the formulae IIIa and IIId, the radical E occurs twice (a=2), then the radicals E can be either identical or different from each other. Similarly, in the formula IIIc, the radicals D can be identical or different.

Useful dyes of this class for hair dyeing are for example water-soluble azo dyes, especially monoazo dyes of the formula IIIa (a=1), disazo dyes of the formula IIIa (a=2) or IIIb or trisazo dyes of the formula IIIc or IIId which have hydroxysulfonyl and/or carboxyl groups.

Important coupling components HK are derived for example from compounds of the benzene, naphthalene, pyrazole, pyridine, pyrimidine, indole or N-arylacetoacetamide series.

Important diazo components D—NH$_2$ are derived for example from compounds of the aniline or aminonaphthalene series. It is possible to use them as coupling components at the same time. So the terms diazo and coupling component are not mandatory for the preparative process, but merely reflect one possible process.

W in the formula I is further for example, in case 2), the optionally metallized radical of an azo dye. Suitable azo dyes from which such radicals W are derived are known per se and have been described in large numbers, for example in K. Venkataraman, The Chemistry of Synthetic Dyes, Vol. VI, Academic Press, New York, London, 1972. Suitable azo dyes conform for example to the formula IV

D—N=N—K(—N=N—D)$_l$        (IV), where D is the radical of a diazo component, K is the radical of a coupling component and l is 0 or 1 and where, when l is 1, the radicals D are identical or different from each other.

Useful dyes from which the radical W is derived include for example water-soluble azo dyes, especially monoazo dyes of the formula IV (l=0) which may have hydroxysulfonyl and/or carboxyl groups.

The radical W is preferably derived from unmetallized azo dyes, especially from those containing sulfonic acid and/or carboxyl groups, of which those having from 1 to 6 sulfonic acid groups are to be particularly emphasized.

Important azo dyes from which the radical W is derived not only in case 1) but also in case 2) are for example those of the phenyl-azo-naphthalene, phenyl-azo-1-phenylpyrazol-5-one, phenyl-azo-benzene, naphthyl-azo-benzene, phenyl-azo-aminonaphthalene, naphthyl-azo-naphthalene, naphthyl-azo-1-phenylpyrazol-5-one, phenyl-azo-pyridone, phenyl-azo-aminopyridine, naphthyl-azo-pyridone, naphthyl-azo-aminopyridine or stilbyl-azo-benzene series.

Radicals D of diazo components of the aniline or aminonaphthalene series which do not bear fiber-reactive groups are derived for example from amines of the formulae Va–f

(Va)

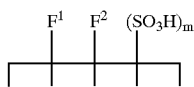

(Vb)

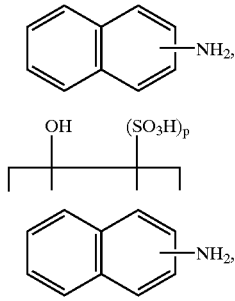

(Vc)

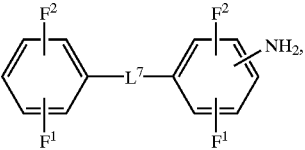

(Vd)

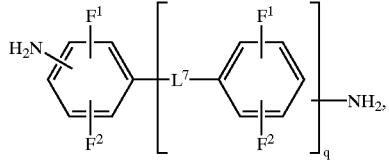

(Ve)

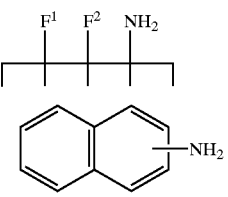

(Vf)

where
m is 0, 1, 2 or 3,
p is 0, 1 or 2,
q is 0 or 1,
F$^1$ is hydrogen, C$_1$–C$_4$-alkyl, C$_1$–C$_4$-alkoxy, acetyl, cyano, carboxyl, hydroxysulfonyl, C$_1$–C$_4$-alkoxycarbonyl, hydroxyl, carbamoyl, mono- or di-(C$_1$–C$_4$)alkylcarbamoyl, fluorine, chlorine, bromine or trifluoromethyl,
F$^2$ is hydrogen, C$_1$–C$_4$-alkyl, C$_1$–C$_4$-alkoxy, cyano, carboxyl, hydroxysulfonyl, acetylamino, C$_1$–C$_4$-alkoxycarbonyl, carbamoyl, mono- or di-(C$_1$–C$_4$) alkylcarbamoyl, fluorine, chlorine, nitro, sulfamoyl, C$_1$–C$_4$-mono- or dialkylsulfamoyl, C$_1$–C$_4$-alkylsulfonyl, phenylsulfonyl or phenoxy and
L$^7$ is a direct bond, oxygen,-sulfur or a radical of the formula —NHCO—, —NHCONH—, —CONH—, —CO—, —NHSO$_2$—, —SO$_2$NH—, —SO$_2$—, —CH=CH—, —CH$_2$—CH$_2$—, —CH$_2$—, —NH—, or —N=N—.

Preference is given to those components in which F$^1$ is hydrogen, methyl, methoxy, carboxyl, hydroxysulfonyl, hydroxyl or chlorine, F$^2$ is hydrogen, methyl, methoxy, carboxyl, hydroxysulfonyl, acetylamino or chlorine, and L$^7$ is a radical of the formula —CO—, —SO$_2$—, —CH=CH—, —CH$_2$—CH$_2$—, —CH$_2$— or —N=N—.

Aromatic amines suitable for use as diazo components and conforming to the formula Va, Vb, Vc or Vd include for example aniline, 2-methoxyaniline, 2-methylaniline, 4-chloro-2-aminoanisole, 4-methylaniline, 4-methoxyaniline, 2-methoxy-5-methylaniline, 2,5-dimethoxyaniline, 2,5-dimethylaniline, 2,4-dimethylaniline, 2,5-diethoxyaniline, 2-chloroaniline, 3-chloroaniline, 4-chloroaniline, 2,5-dichloroaniline, 4-chloro-2-nitroaniline, 4-chloro-2-methylaniline, 3-chloro-2-methylaniline, 4-chloro-2-aminotoluene, 4-phenylsulfonylaniline, 2-ethoxy-1-naphthylamine, 1-naphthylamine, 2-naphthylamine, 4-methylsulfonylaniline, 2,4-dichloroaniline-5-carboxylic acid, 2-aminobenzoic acid, 4-aminobenzoic acid, 3-aminobenzoic acid, 3-chloroaniline-6-carboxylic acid, aniline-2- or -3- or -4-sulfonic acid, aniline-2,5-disulfonic acid, aniline-2,4-disulfonic acid, aniline-3,5-disulfonic acid, 2-aminotoluene-4-sulfonic acid, 2-aminoanisole-4-sulfonic acid, 2-aminoanisole-5-sulfonic acid, 2-ethoxyaniline-5-sulfonic acid, 2-ethoxyaniline-4-sulfonic acid, 4-hydroxysulfonyl-2-aminobenzoic acid, 2,5-dimethoxyaniline-4-sulfonic acid, 2,4-dimethoxyaniline-5-sulfonic acid, 2-methoxy-5-methylaniline-4-sulfonic acid, 4-aminoanisole-3-sulfonic acid, 4-aminotoluene-3-sulfonic acid, 2-aminotoluene-5-sulfonic acid, 2-chloroaniline-4-sulfonic acid, 2-chloroaniline-5-sulfonic acid, 2-bromoaniline-4-sulfonic acid, 2,6-dichloroaniline-4-sulfonic acid, 2,6-dimethylaniline-3- or -4-sulfonic acid, 3-acetylaminoaniline-6-sulfonic acid, 4-acetylaminoaniline-2-sulfonic acid, 1-aminonaphthalene-4-sulfonic acid, 1-aminonaphthalene-3-sulfonic acid, 1-aminonaphthalene-5-sulfonic acid, 1-aminonaphthalene-6-sulfonic acid, 1-aminonaphthalene-7-sulfonic acid, 1-aminonaphthalene-3,7-disulfonic acid, 1-aminonaphthalene-3,6,8-trisulfonic acid, 1-aminonaphthalene-4,6,8-trisulfonic acid, 2-naphthylamine-5- or -6- or -8-sulfonic acid, 2-aminonaphthalene-3,6,8-trisulfonic acid, 2-aminonaphthalene-6,8-disulfonic acid, 2-aminonaphthalene-1,6-disulfonic acid, 2-aminonaphthalene-1-sulfonic acid, 2-aminonaphthalene-1,5-disulfonic acid, 2-aminonaphthalene-3,6-disulfonic acid, 2-aminonaphthalene-4,8-disulfonic acid, 2-aminophenol-4-sulfonic acid, 2-aminophenol-5-sulfonic acid, 3-aminophenol-6-sulfonic acid, 1-hydroxy-2-aminonaphthalene-5,8- or -4,6-disulfonic acid, 4-aminodiphenylamine, 4-amino-4'-methoxydiphenylamine, 4-amino-4'-methoxydiphenylamine-3-sulfonic acid, 4-(2'-methylphenylazo)-2-methylaniline, 4-aminoazobenzene, 4'-nitrophenylazo-1-aminonaphthalene, 4-(6'-hydroxysulfonylnaphthylazo)-1-aminonaphthalene, 4-(2',5'-dihydroxysulfonylphenylazo)-1-aminonaphthalene, 4'-amino-3'-methyl-3-nitrobenzophenone, 4-aminobenzophenone, 4-(4'-aminophenylazo) benzenesulfonic acid, 4-(4'-amino-3'-methoxyphenylazo) benzenesulfonic acid or 2-ethoxy-1-naphthylamine-6-sulfonic acid.

Aromatic diamines suitable for use as tetraazo components or else for doubling (eg. with cyanuric chloride) and conforming to the formula Ve or Vf include for example 1,3-diaminobenzene, 1,3-diaminobenzene-4-sulfonic acid, 1,4-diaminobenzene, 1,4-diaminobenzene-2-sulfonic acid, 1,4-diamino-2-methylbenzene, 1,4-diamino-2-methoxybenzene, 1,3-diamino-4-methylbenzene, 1,3-diaminobenzene-5-sulfonic acid, 1,3-diamino-5-methylbenzene, 1,6-diaminonaphthalene-4-sulfonic acid, 2,6-diaminonaphthalene-4,8-disulfonic acid, 3,3'-diaminodiphenyl sulfone, 4,4'-diaminodiphenyl sulfone, 4,4'-diaminostilbene-2,2'-disulfonic acid, 2,2'-diaminodiphenyl sulfone, 2,2'-sulfonyldianiline-4,5-disulfonic acid, 4,4'-diaminobenzophenone, 4,4'-diamino-3,3'-dinitrobenzophenone, 3,3'-diamino-4,4'-dichlorobenzophenone, 4,4'- or 3,3'-diaminobiphenyl, 4,4'-diamino-3,3'-dichlorobiphenyl, 4,4'-diamino-3,3'-dimethoxy- or -3,3'-dimethyl- or -2,2'-dimethyl- or -2,2'-dichloro- or -3,3'-diethoxy-biphenyl, 4,4'-diamino-3,3'-dimethyl-6,6'-dinitrobiphenyl, 4,4'-diaminobiphenyl-2,2'- or -3,3'-disulfonic acid, 4,4'-diamino-3,3'-dimethyl- or -3,3'-dimethoxy- or -2,2'-dimethoxy-biphenyl-6,6'-disulfonic acid, 4,4'-diamino-2,2',5,5'-tetrachlorobiphenyl, 4,4'-diamino-3,3'-dinitrobiphenyl, 4,4'-diamino-2,2'-dichloro-5,5'-dimethoxybiphenyl, 4,4'-diaminobiphenyl-2,2'- or -3,3'-dicarboxylic acid, 4,4'-diamino-3,3'-dimethylbiphenyl-5,5'-disulfonic acid, 4,4'-diamino-2-nitrobiphenyl, 4,4'-diamino-3-ethoxy- or -3-hydroxy-sulfonylbiphenyl, 4,4'-diamino-3,3'-dimethylbiphenyl-5-sulfonic acid, 4,4'-diaminodiphenylmethane, 4,4'-diamino-3,3'-dimethyldiphenylmethane, 4,4'-diamino-2,2',3,3'-tetramethyldiphenylmethane, 4,4'-diaminodiphenylethane, 4,4'-diaminostilbene or 4,4'-diaminodiphenylmethane-3,3'-dicarboxylic acid.

Aromatic radicals D of diazo components of the aniline or aminonaphthalene series which bear further fiber-reactive radicals are derived for example from amines of the formulae VIa–c

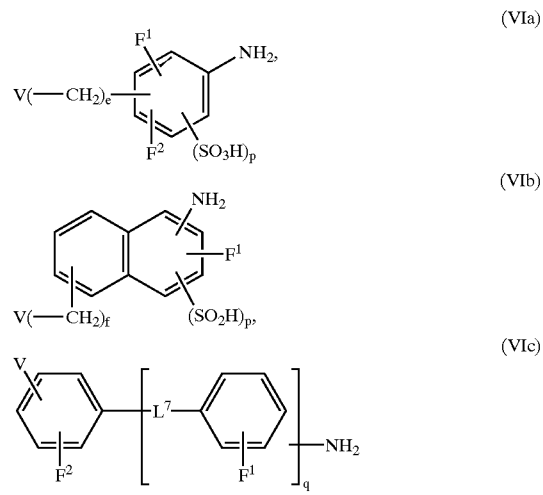

where $F^1$, $F^2$, p, q and $L^7$ are each as defined above, e and f are identical or different and each is independently of the other 0 or 1, and V is a fiber-reactive radical.

Fiber-reactive radicals V are derived for example from the radical E or are, as observed above, other additively or substitutively reacting fiber-reactive radicals.

Aromatic amines which form the basis of the derivatives of the formula VIa, VIb or VIc which have a fiber-reactive radical V include for example 1,3-diaminobenzene, 1,3-diaminobenzene-4-sulfonic acid, 1,3-diaminobenzene-4,6-disulfonic acid, 1,4-diaminobenzene, 1,4-diaminobenzene-2-sulfonic acid, 1,4-diaminobenzene-2,5-disulfonic acid, 1,4-diamino-2-methylbenzene, 1,4-diamino-2-methoxybenzene, 1,3-diamino-4-methylbenzene, 1,4-diaminobenzene-2,6-disulfonic acid, 1,5-diamino-4-methylbenzene-2-sulfonic acid, 1,5-diamino-4-methoxybenzene-2-sulfonic acid, 1,6-diaminonaphth-2-ol-4-sulfonic acid, 1,6-diaminonaphthalene-4-sulfonic acid, 2,6-diaminonaphthalene-4,8-disulfonic acid, 2,6-diaminonaphth-1-ol-4,8-disulfonic acid, 1,3-diaminobenzene-5-sulfonic acid, 1,3-diamino-5-methylbenzene, 2,6-diaminophenol-4-sulfonic acid, 5-aminomethyl-2-aminonaphthalene-1-sulfonic acid, 5-(N-methylaminomethyl)-2-aminonaphthalene-1-sulfonic acid, 4,4'-diaminostilbene-3,3'-dicarboxylic acid, 4-(N-methylaminomethyl)aniline-2-sulfonic acid or 3-(N-methylaminomethyl)aniline-6-sulfonic acid.

The radicals K of the coupling component are preferably selected from the benzene, naphthalene, pyrazole, pyridine, pyrimidine, indole or N-arylacetoacetamide series and may also bear fiber-reactive groups.

Coupling components free of fiber-reactive groups are preferably compounds of the naphthalene, aniline, pyrazolone, aminopyrazole, 2,6-diaminopyridine, pyridone, hydroxypyrimidine, indole, N-arylacetoacetamide series and correspond for example to the compounds of the formulae VII a–m

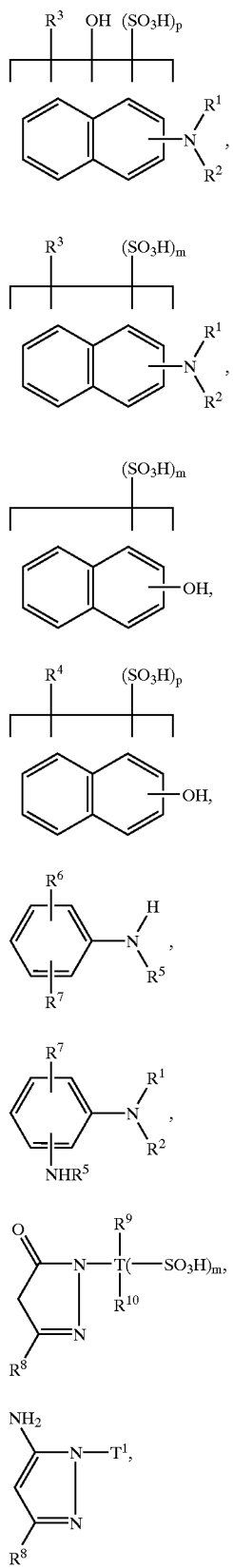
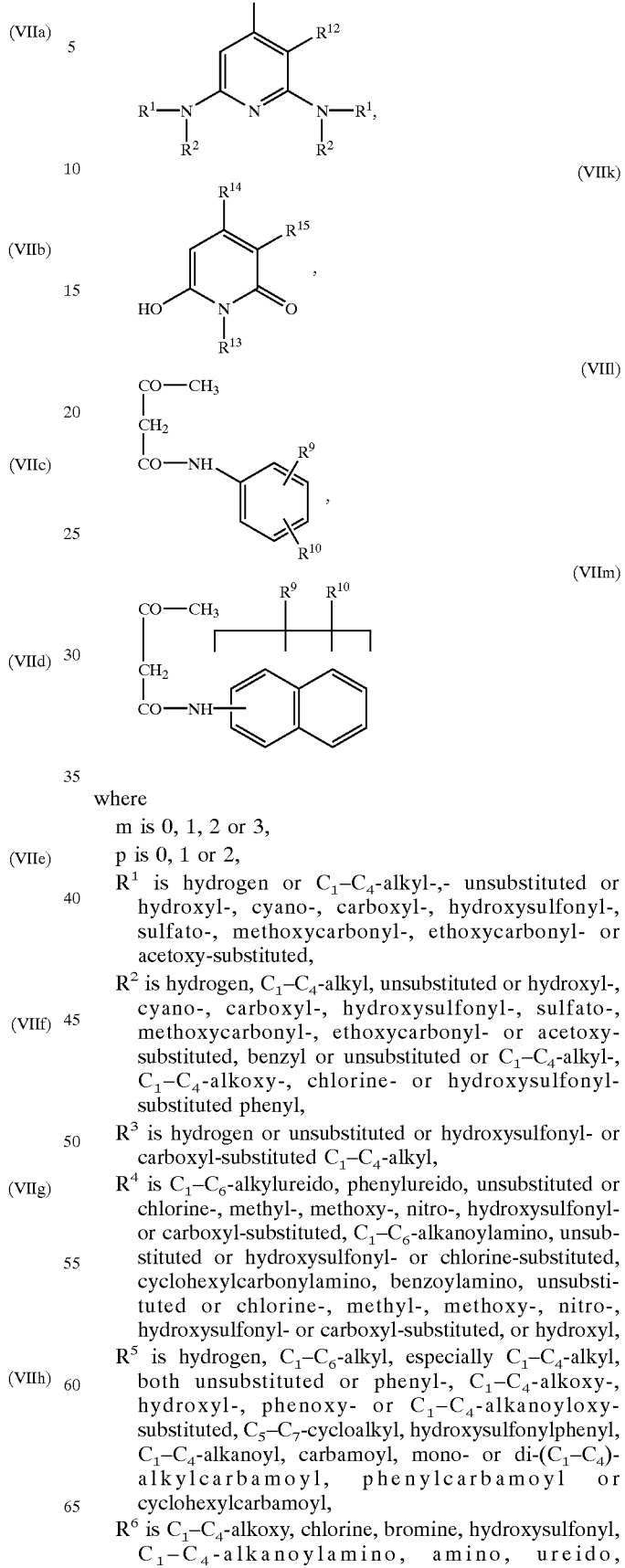

where
m is 0, 1, 2 or 3,
p is 0, 1 or 2,
$R^1$ is hydrogen or $C_1$–$C_4$-alkyl,- unsubstituted or hydroxyl-, cyano-, carboxyl-, hydroxysulfonyl-, sulfato-, methoxycarbonyl-, ethoxycarbonyl- or acetoxy-substituted,
$R^2$ is hydrogen, $C_1$–$C_4$-alkyl, unsubstituted or hydroxyl-, cyano-, carboxyl-, hydroxysulfonyl-, sulfato-, methoxycarbonyl-, ethoxycarbonyl- or acetoxy-substituted, benzyl or unsubstituted or $C_1$–$C_4$-alkyl-, $C_1$–$C_4$-alkoxy-, chlorine- or hydroxysulfonyl-substituted phenyl,
$R^3$ is hydrogen or unsubstituted or hydroxysulfonyl- or carboxyl-substituted $C_1$–$C_4$-alkyl,
$R^4$ is $C_1$–$C_6$-alkylureido, phenylureido, unsubstituted or chlorine-, methyl-, methoxy-, nitro-, hydroxysulfonyl- or carboxyl-substituted, $C_1$–$C_6$-alkanoylamino, unsubstituted or hydroxysulfonyl- or chlorine-substituted, cyclohexylcarbonylamino, benzoylamino, unsubstituted or chlorine-, methyl-, methoxy-, nitro-, hydroxysulfonyl- or carboxyl-substituted, or hydroxyl,
$R^5$ is hydrogen, $C_1$–$C_6$-alkyl, especially $C_1$–$C_4$-alkyl, both unsubstituted or phenyl-, $C_1$–$C_4$-alkoxy-, hydroxyl-, phenoxy- or $C_1$–$C_4$-alkanoyloxy-substituted, $C_5$–$C_7$-cycloalkyl, hydroxysulfonylphenyl, $C_1$–$C_4$-alkanoyl, carbamoyl, mono- or di-($C_1$–$C_4$)-alkylcarbamoyl, phenylcarbamoyl or cyclohexylcarbamoyl,
$R^6$ is $C_1$–$C_4$-alkoxy, chlorine, bromine, hydroxysulfonyl, $C_1$–$C_4$-alkanoylamino, amino, ureido, methylsulfonylamino, ethylsulfonylamino, dimethylaminosulfonylamino, methylamino, ethylamino, dimethylamino or diethylamino, $R^7$ is hydrogen, $C_1$–$C_4$-alkyl, $C_1$–$C_4$-alkoxy, hydroxysulfonyl, chlorine or bromine, T is the radical of a benzene or naphthalene ring, $T^1$ is $C_1$–$C_4$-alkyl, cyclohexyl, benzyl or unsubstituted or fluorine-, chlorine-, bromine-, methoxy-, nitro-, hydroxysulfonyl-, carboxyl-, acetyl-, acetylamino-, methylsulfonyl-, sulfamoyl- or carbamoyl-monosubstituted, -disubstituted or -trisubstituted phenyl, $R^8$ is methyl, carboxyl, $C_1$–$C_4$-alkoxycarbonyl or phenyl, $R^9$ is hydrogen, $C_1$–$C_4$-alkyl, $C_1$–$C_4$-alkoxy, acetyl, cyano, carboxyl, hydroxysulfonyl, $C_1$–$C_4$-alkoxycarbonyl, hydroxyl, carbamoyl, mono- or di-$C_1$–$C_4$-alkylcarbamoyl, fluorine, chlorine, bromine or trifluoromethyl, $R^{10}$ is hydrogen, $C_1$–$C_4$-alkyl, $C_1$–$C_4$-alkoxy, cyano, carboxyl, hydroxysulfonyl, acetylamino, $C_1$–$C_4$-alkoxycarbonyl, carbamoyl, mono- or di-($C_1$–$C_4$)-alkylcarbamoyl, fluorine, chlorine, nitro, sulfamoyl, mono- or di-($C_1$–$C_4$)-alkylsulfamoyl, $C_1$–$C_4$-alkylsulfonyl, phenylsulfonyl or phenoxy, $R^{11}$ is hydrogen or unsubstituted or $C_1$–$C_4$-alkoxy- or cyano-substituted $C_1$–$C_4$-alkyl, $R^{12}$ is hydrogen, methyl, hydroxysulfonylmethyl, hydroxysulfonyl, cyano or carbamoyl, $R^{13}$ is hydrogen, $C_1$–$C_4$-alkyl, unsubstituted or phenyl-, hydroxysulfonylphenyl-, hydroxyl-, amino-, $C_1$–$C_4$-alkoxy-, carboxyl-, hydroxysulfonyl-, acetylamino-, benzoylamino- or cyano-substituted, cyclohexyl, phenyl, unsubstituted or carboxyl-, hydroxysulfonyl-, benzoylamino-, acetylamino-, methyl-, methoxy-, cyano- or chlorine-substituted, or phenyl-, $C_1$–$C_4$-alkyl-, $C_1$–$C_4$-alkanoyl- or benzoyl-substituted amino, $R^{14}$ is hydrogen, $C_1$–$C_4$-alkyl, phenyl, hydroxyl, cyano, acetyl, benzoyl, carboxyl, methoxycarbonyl, carbamoyl or hydroxysulfonylmethyl and $R^{15}$ is hydrogen, chlorine, bromine, acetylamino, amino, nitro, hydroxysulfonyl, sulfamoyl, methylsulfonyl, phenylsulfonyl, carboxyl, $C_1$–$C_4$-alkoxycarbonyl, $C_1$–$C_4$-alkanoyl, benzoyl, carbamoyl, cyano or hydroxysulfonylmethyl.

$U^2$, $U^3$, $F^1$, $F^2$, $R^1$, $R^2$, $R^3$, $R^5$, $R^7$, $T^1$, $R^9$, $R^{10}$, $R^{11}$, $R^{13}$ and $R^{14}$ and also the below-described radicals $G^3$, $G^5$, $G^{12}$ and $G^{13}$ are each for example methyl, ethyl, propyl, isopropyl, butyl, isobutyl, sec-butyl or tert-butyl.

$U^2$, $U^3$ and $R^5$ may each also be pentyl, isopentyl, neopentyl, tert-pentyl, hexyl or 2-methylpentyl.

$U^2$, $U^3$, $R^1$, $R^2$, $R^5$ and $R^{13}$ are each hydroxy-$C_1$–$C_4$-alkyl such as hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 1-hydroxybut-3-yl, 2-hydroxybut-3-yl, 1-hydroxy-2-methylprop-3-yl, 2-hydroxy-2-methylprop-3-yl, 3-hydroxy-2-methylprop-3-yl or 2-hydroxymethylprop-2-yl.

$U^2$, $U^3$, $R^1$, $R^2$, $R^{11}$ and $R^{13}$ may each also be for example cyanomethyl, cyanoethyl, cyanopropyl or cyanobutyl.

$R^1$, $R^2$, $R^3$ and $R^{13}$ are each for example carboxymethyl, carboxyethyl, 2- or 3-carboxypropyl or 2- or 4-carboxybutyl.

$U^2$, $U^3$, $R^1$, $R^2$ and $R^3$ may each also be for example hydroxysulfonylmethyl, 2-hydroxysulfonylethyl, 2- or 3-hydroxysulfonylpropyl, 2- or 4-hydroxysulfonylbutyl.

$R^1$ and $R^2$ may each also be for example 2-sulfatoethyl, 2- or 3-sulfatopropyl, 2- or 4-sulfatobutyl, methoxycarbonylmethyl, 2-methoxycarbonylethyl, 2- or 3-methoxycarbonylpropyl, 2- or 4-methoxycarbonylbutyl, ethoxycarbonylmethyl, 2-ethoxycarbonylethyl, 2- or 3-ethoxycarbonylpropyl, 2- or 4-ethoxycarbonylbutyl, acetoxymethyl, 2-acetoxyethyl, 2- or 3-acetoxypropyl, 2- or 4-acetoxybutyl.

$R^2$ may also be for example 2-, 3- or 4-methylphenyl, 2-, 3- or 4-ethylphenyl, 2-, 3- or 4-propylphenyl, 2-, 3- or 4-isopropylphenyl, 2-, 3- or 4-butylphenyl, 2-, 3- or 4-isobutylphenyl, 2-, 3- or 4-sec-butylphenyl, 2-, 3- or 4-tert-butylphenyl, 2-, 3- or 4-methoxyphenyl, 2-, 3- or 4-ethoxyphenyl, 2-, 3- or 4-propoxyphenyl, 2-, 3- or 4-isopropoxyphenyl, 2-, 3- or 4-butoxyphenyl, 2-, 3- or 4-isobutoxyphenyl, 2-, 3- or 4-sec-butoxyphenyl, 2-, 3- or 4-tert-butoxyphenyl, 2-, 3- or 4-chlorophenyl.

$R^2$, $R^5$ and $T^1$ may each also be for example 2-, 3- or 4-hydroxysulfonylphenyl.

$R^4$ is for example methylureido, ethylureido, propylureido, butylureido, pentylureido, hexylureido, formylamino, acetylamino, propionylamino, butyrylamino, isopropylcarbonylamino, valerylamino, isobutylcarbonylamino, sec-butylcarbonylamino, tert-butylcarbonylamino, pentylcarbonylamino.

$R^5$ and $R^{13}$ are each for example benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 3-phenylbut-2-yl, 4-phenylbut-2-yl, 1-(phenylmethyl)-eth-1-yl, 1-(phenylmethyl)-1-(methyl)-eth-1-yl or 1-(phenylmethyl)-prop-1-yl, preferably benzyl or 2-phenylethyl.

$R^5$, $R^{11}$ and $R^{13}$ may each also be for example methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl.

$R^5$ can also be for example phenoxymethyl, 2-phenoxyethyl, 2- or 3-phenoxypropyl, 2- or 4-phenoxybutyl, formyloxymethyl, 2-(formyloxy)ethyl, 3-(formyloxy)propyl, 2- or 4-(formyloxy)butyl, methylcarbonyloxymethyl, 2-(methylcarbonyloxy)ethyl, 2- or 3-(methylcarbonyloxy)propyl, 2- or 4-(methylcarbonyloxy)butyl, ethylcarbonyloxymethyl, 2-(ethylcarbonyloxy)ethyl, 2- or 3-(ethylcarbonyloxy)

propyl, 2- or 4-(ethylcarbonyloxy)butyl, propylcarbonyloxymethyl, 2-(propylcarbonyloxy)ethyl, 2- or 3-(propylcarbonyloxy)propyl, 2- or 4-(propylcarbonyloxy)butyl, cyclopentyl, cyclohexyl, cycloheptyl.

$R^5$, $R^{15}$ and also the below-described radicals $G^4$ are each for example formyl, acetyl, propionyl, butyryl, isobutyryl.

$F^1$, $F^2$, $R^5$, $R^9$, $R^{10}$ and also the below-described radicals $G^4$ are each for example mono- or dimethylcarbamoyl, mono- or diethylcarbamoyl, mono- or dipropylcarbamoyl, mono- or dibutylcarbamoyl.

$F^1$, $F^2$, $R^6$, $R^7$, $R^9$, $R^{10}$ and also the below-described radicals $G^3$ and $G^5$ can each also be for example methoxy, ethoxy, propoxy, isopropoxy, butoxy, sec-butoxy, isobutoxy, tert-butoxy.

$R^6$ and $R^{13}$ are each for example formylamino, methylcarbonylamino, ethylcarbonylamino, propylcarbonylamino, isopropylcarbonylamino.

$T^1$ may also be for example 2-, 3- or 4-fluorophenyl, 2-, 3- or 4-chlorophenyl, 2-, 3- or 4-bromophenyl, 2-, 3- or 4-methoxyphenyl, 2-, 3- or 4-nitrophenyl, 2-, 3- or 4-carboxyphenyl, 2-, 3- or 4-acetylphenyl, 2-, 3- or 4-acetylaminophenyl, 2-, 3- or 4-methylsulfonylphenyl, 2-, 3- or 4-sulfamoylphenyl or 2-, 3- or 4-carbamoylphenyl.

$F^1$, $F^2$, $R^8$, $R^9$, $R^{10}$, $R^{15}$ and also the below-described radicals $R^{16}$ may also be for example methoxycarbonyl, ethoxycarbonyl, propoxycarbonyl, isopropoxycarbonyl, butoxycarbonyl, isobutoxycarbonyl, sec-butoxycarbonyl or tert-butoxycarbonyl.

$F^2$ and $R^{10}$ may also be for example mono- or dimethylsulfamoyl, mono- or diethylsulfamoyl, mono- or dipropylsulfamoyl, mono- or dibutylsulfamoyl, methylsulfonyl, ethylsulfonyl, propylsulfonyl or butylsulfonyl.

$R^{13}$ may also be for example hydroxysulfonylphenylmethyl, 2-hydroxysulfonylphenylethyl, 2- or 3-hydroxysulfonylphenylpropyl, 2- or 4-hydroxysulfonylphenylbutyl, aminomethyl, 2-aminoethyl, 2- or 3-aminopropyl, 2- or 4-aminobutyl, hydroxysulfonylmethyl, 2-hydroxysulfonylethyl, 2- or 3-hydroxysulfonylpropyl, 2- or 4-hydroxysulfonylbutyl, acetylaminomethyl, 2-acetylaminoethyl, 2- or 3-acetylaminopropyl, 2- or 4-acetylaminobutyl, benzoylaminomethyl, 2-benzoylaminoethyl, 2- or 3-benzoylaminopropyl, 2- or 4-benzoylaminobutyl, 2-, 3- or 4-carboxyphenyl, 2-, 3- or 4-hydroxysulfonylphenyl, 2-, 3- or 4-benzoylaminophenyl, 2-, 3- or 4-acetylaminophenyl, 2-, 3- or 4-methylphenyl, 2-, 3- or 4-methoxyphenyl, 2-, 3- or 4-cyanophenyl, 2-, 3- or 4-chlorophenyl, phenylamino, methylamino, ethylamino, propylamino, isopropylamino, butylamino, isobutylamino, sec-butylamino, tert-butylamino or benzoylamino.

The radicals $L^5$ and also the below-described radicals $L^8$ are each for example $(CH_2)_2$, $(CH_2)_3$, $(CH_2)_4$, $CH(CH_3)CH_2$, $CH(CH_3)CH(CH_3)$, $(CH_2)_5$ or $(CH_2)_6$.

$L^5$ may also be for example $(CH_2)_2O(CH_2)_2$, $(CH_2)_3O(CH_2)_2$, $(CH_2)_2O(CH_2)_2O(CH_2)_2$, $(CH_2)_2S(CH_2)_2$, $(CH_2)_3S(CH_2)_2$, $(CH_2)_2S(CH_2)_2S(CH_2)_2$, $(CH_2)_2NH(CH_2)_2$, $(CH_2)_3NH(CH_2)_2$, $(CH_2)_2NH(CH_2)_2NH(CH_2)_2$,

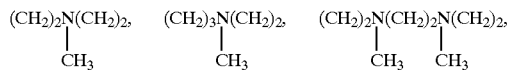

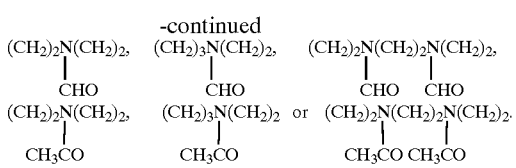

$L^6$ and $L^{11}$ are each $CH_2$, $(CH_2)_2$, $(CH_2)_3$, $(CH_2)_4$, $CH(CH_3)CH_2$ or $CH(CH_3)CH(CH_3)$.

In what follows, coupling components KH are recited by way of example. Specific examples of naptholsulfonic acids are 1-naphthol-3-sulfonic acid, 1-naphthol-4-sulfonic acid, 1-naphthol-5-sulfonic acid, 1-naphthol-8-sulfonic acid, 1-naphthol-3,6-disulfonic acid, 1-naphthol-3,8-disulfonic acid, 2-naphthol-5-sulfonic acid, 2-naphthol-6-sulfonic acid, 2-naphthol-7-sulfonic acid, 2-naphthol-8-sulfonic acid, 2-naphthol-3,6-disulfonic acid, 2-naphthol-6,8-disulfonic acid, 2-naphthol-3,6,8-trisulfonic acid, 1,8-dihydroxynaphthalene-3,6-disulfonic acid, 2,6-dihydroxynapthalene-8-sulfonic acid and 2,8-dihydroxynaphthalene-6-sulfonic acid.

Further examples are 1-naphthylamine, N-phenyl-1-naphthylamine, N-ethyl-1-naphthylamine, N-phenyl-2-naphthylamine, 1-naphthol, 2-naphthol, 1,5-dihydroxynaphthalene, 1,6-dihydroxynaphthalene, 1,7-dihydroxynaphthalene and 2,7-dihydroxynaphthalene.

Examples of aminonaphthalenesulfonic acids are 1-naphthylamine-6-sulfonic acid, 1-naphthylamine-7-sulfonic acid, 1-naphthylamine-8-sulfonic acid, 2-naphthylamine-3,6-disulfonic acid, 2-naphthylamine-5,7-disulfonic acid, 2-naphthylamine-6,8-disulfonic acid, 2-hydroxysulfonylmethylaminonaphthalene-5-sulfonic acid and 2-hydroxysulfonylmethylaminonaphthalene-6-sulfonic acid.

Examples of aminonaphtholsulfonic acids are 1-amino-5-hydroxynaphthalene-7-sulfonic acid, 1-amino-8-hydroxynaphthalene-4-sulfonic acid, 1-amino-8-hydroxynaphthalene-2,4-disulfonic acid, 1-amino-8-hydroxynaphthalene-3,6-disulfonic acid, 1-amino-8-hydroxynaphthalene-4,6-disulfonic acid, 2-amino-5-hydroxynaphthalene-7-sulfonic acid, 2-amino-8-hydroxynaphthalene-6-sulfonic acid, 2-amino-8-hydroxynaphthalene-3,6-disulfonic acid, 2-amino-5-hydroxynaphthalene-1,7-disulfonic acid, 3-amino-7-hydroxysulfonylmethyl-8-hydroxynaphthalene-3,6-disulfonic acid, 2-amino-7-hydroxysulfonylmethyl-8-hydroxynaphthalene-6-sulfonic acid, 1-acetylamino-8-hydroxynaphthalene-3,6-disulfonic acid, 1-benzoylamino-8-hydroxynaphthalene-3,6-disulfonic acid 1-acetylamino-8-hydroxynaphthalene-4,6-disulfonic acid, 1-benzoylamino-8-hydroxynaphthalene-4,6-disulfonic acid, 1-acetylamino-5-hydroxynaphthalene-7-sulfonic acid, 2-methylamino-8-hydroxynaphthalene-6-sulfonic acid, 2-methylamino-8-hydroxynaphthalene-6-sulfonic acid, 2-hydroxysulfonylmethylamino-8-hydroxynaphthalene-6-sulfonic acid, 2-hydroxysulfonylmethylamino-7-hydroxysulfonylmethyl-8-hydroxynaphthalene-6-sulfonic acid, 2-hydroxysulfonylmethylamino-8-hydroxynaphthalene-3,6-disulfonic acid, 2-hydroxysulfonylmethylamino-7-hydroxysulfonylmethyl-8-hydroxynaphthalene-3,6-disulfonic acid, 2-(3'- or 4'-hydroxysulfonylphenylamino)-8-hydroxynaphthalene-6-sulfonic acid, 2-acetylamino-5-hydroxynaphthalene-7-sulfonic acid and 2-acetylamino-8-hydroxynaphthalene-6-sulfonic acid.

Examples of benzene coupling components are o- or m-toluidine, o- or m-anisidine, cresidine, 2,5- dimethylaniline, 2,5-dimethoxyaniline, m-aminoacetanilide, 3-amino-4-methoxyacetanilide, 3amino-4-methylacetanilide, m-aminophenylurea, N-methylaniline, N-methyl-m-toluidine, N-ethylaniline, N-ethyl-m-toluidine, N-(2-hydroxyethyl)aniline and N-(2-hydroxyethyl)-m-toluidine.

Examples of pyrazolone coupling components are 3-methyl-, 3-carboxy- or 3-($C_1$–$C_4$-alkoxycarbonyl)-pyrazol-5-ones with or without substitution in position 1 by unsubstituted or methyl-, ethyl-, fluorine-, chlorine-, bromine-, trifluoromethyl-, methoxy-, ethoxy-, cyano-, phenoxy-, phenylsulfonyl-, methylsulfonyl-, hydroxysulfonyl-, acetylamino-, nitro-, hydroxyl-, carboxyl-, carbamoyl- or sulfamoyl-substituted phenyl or by hydroxysulfonyl-substituted 1- or 2-naphthyl. Examples are 1-phenyl-, 1-(2'-chlorophenyl)-, 1-(2'-methoxyphenyl)-, 1-(2'-methylphenyl)-, 1-(1',5'-dichlorophenyl)-, 1-(2',6'-dichlorophenyl)-, 1-(2'-methyl-6'-chlorophenyl)-, 1-(2'-methoxy-5'-methylphenyl)-, 1-(2'-methoxy-5'-hydroxysulfonylphenyl)-, 1-(2',5'-dichloro-4'-hydroxysulfonylphenyl)-, 1-(2',5'-dihydroxysulfonylphenyl)-, 1-(2'-carboxyphenyl)-, 1-(3'-hydroxysulfonylphenyl)-, 1-(4'-hydroxysulfonylphenyl)- or 1-(3'-sulfamoylphenyl)-3-carboxypyrazol-5-one, 1-(3'- or 4'-hydroxysulfonylphenyl)-, 1-(2'-chloro 4'- or -5'-hydroxysulfonylphenyl)-, 1-(2'-methyl-4'-hydroxysulfonylphenyl)-, 1-(2',5'-dichlorophenyl)-, 1-(4',8'-dihydroxysulfonyl-1-naphthyl)-, 1-(6'-hydroxysulfonyl-1-naphthyl)-3-methylpyrazol-5-one, ethyl 1-phenylpyrazol-5-one-3-carboxylate, ethyl pyrazol-5-one-3-carboxylate or pyrazol-5-one-3-carboxylic acid.

Other pyrazole coupling components include for example 1-methyl-, 1-ethyl-, 1-propyl-, 1-butyl-, 1-cyclohexyl-, 1-benzyl- or 1-phenyl-5-aminopyrazole, 1-(4'-chlorophenyl)-, 1-(4'-methylphenyl)-5-aminopyrazole or 1-phenyl-3-methyl-5-aminopyrazole.

N-Arylacetoacetamides are particularly acetoacetanilide or its derivatives having one or more substituents selected from the group consisting of chlorine, methyl, ethyl, methoxy, ethoxy, acetylamino, hydroxysulfonyl, carboxyl, carbamoyl and sulfamoyl in the phenyl ring.

Pyridine coupling components are the derivatives described in DE-A-2 260 827, for example.

Suitable pyrimidine coupling components include for example the compounds recited in DE-A-2 202 820, DE-A-2 308 663 or DE-A-3 119 349. Also suitable are barbituric acid and its N-substitution products. Suitable N-substituents include in particular $C_1$–$C_4$-alkyl or phenyl.

Examples of suitable indole coupling components are 2-methylindole, 2-phenylindole, 2-phenylindole-5-sulfonic acid, 1-methyl-2-phenylindole, 1-(2'-hydroxyethyl)-, 1-(2'-carboxyethyl)-, 1-(2'-carbamoylethyl)-2-methylindole or -2-phenylindole.

Examples of suitable pyridone coupling components are 1-ethyl-2-hydroxy-4-methyl-5-carbamoylpyrid-6-one, 1-(2'-hydroxyethyl)-2-hydroxy-4-methyl-5-carbamoylpyrid-6-one, 1-phenyl-2-hydroxy-4-methyl-5-carbamoylpyrid-6-one, 1-ethyl-2-hydroxy-4-methyl-5-cyanopyrid-6-one, 1-ethyl-2-hydroxy-4-methyl-5-hydroxysulfonylmethylpyrid-6-one, 1-methyl-2-hydroxy-4-methyl-5-cyanopyrid-6-one, 1-methyl-2-hydroxy-5-acetylpyrid-6-one, 1,4-dimethyl-2-hydroxy-5-cyanopyrid-6-one, 1,4-dimethyl-5-carbamoylpyrid-6-one, 2,6-dihydroxy-4-ethyl-5-cyanopyridine, 2-hydroxy-4-ethyl-5-carbamoylpyrid-6-one, 1-ethyl-2-hydroxy-4-methyl-5-hydroxysulfonylmethylpyrid-6-one, 1-methyl-2-hydroxy-4-methyl-5-methylsulfonylpyrid-6-one and 1-carboxymethyl-2-hydroxy-4-ethyl-5-phenylsulfonylpyrid-6-one.

Coupling components KH of the naphthalene, benzene, pyrazolone, aminopyrazole, 2,6-diaminopyridine, pyridone, hydroxypyrimidine, aminopyrimidine, indole or N-arylacetoacetamide series which contain a fiber-reactive group include for example compounds of the formulae VIIIa–k

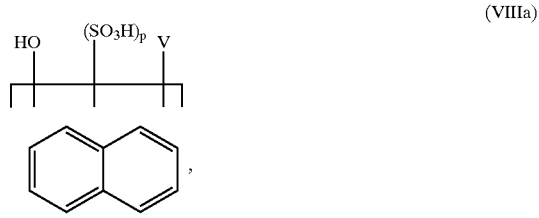

(VIIIa)

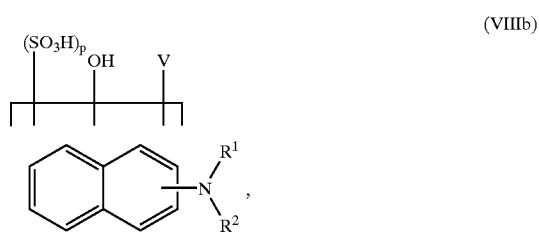

(VIIIb)

(VIIIc)

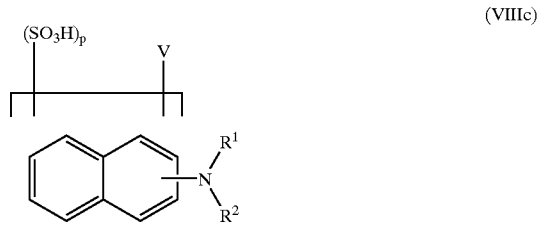

(VIIId)

(VIIIe)

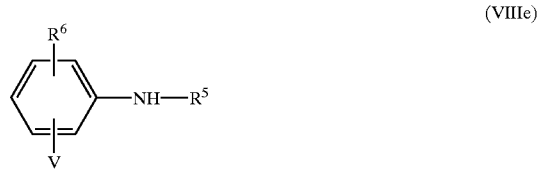

(VIIIf)

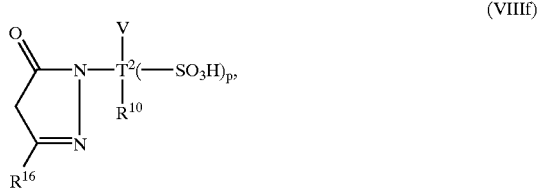

(VIIIg)

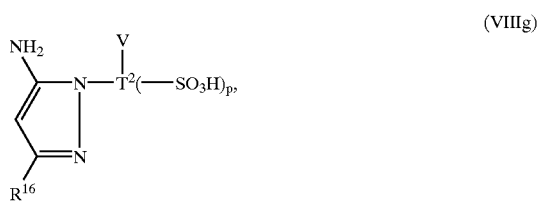

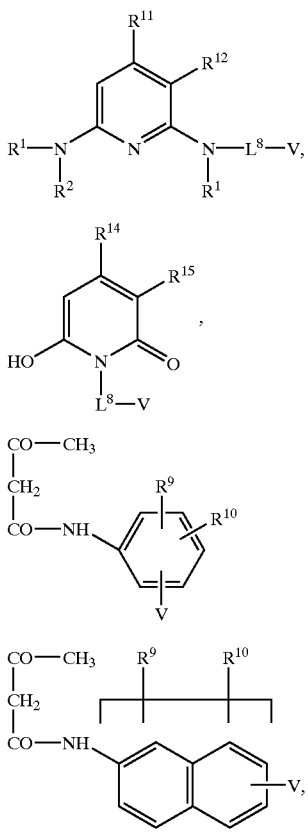

(VIIIh)

(VIIIi)

(VIIIj)

(VIIIk)

where

T² is the radical of a benzene or naphthalene ring,

R¹⁶ is methyl, carboxyl, C₁–C₄-alkoxycarbonyl or phenyl,

L⁸ is C₁–C₆-alkylene, and

R¹, R², R⁵, R⁶, R⁹, R¹⁰, R¹¹, R¹², R¹⁴, R¹⁵, p and V are each as defined above.

Pyrazolone coupling components bearing fiber-reactive radicals V are derived for example from the following pyrazolones: 1-(3'- or 4'-aminophenyl)-, 1-(2'-hydroxysulfonyl-5'-aminophenyl)- or 1-(2'-methoxy-5'-aminophenyl)-3-carboxypyrazol-5-one, 1-(3'- or 4'-aminophenyl)- or 1-(6'-amino-4',8'-dihydroxysulfonylnaphth-2'-yl)-3-carboxypyrazol-5-one.

Particular preference for use in hair dyeing is given to dyes of the formula IX

  E—N=N—K¹   (IX), where E is as defined above and K¹ is the radical of a coupling component of the benzene, naphthalene, pyrazole or pyridine series which optionally has further fiber-reactive groups, especially the group E, the group of the formula SO₂—Y, where Y is as defined above, or those of the halotriazine series.

Particular preference is given to the use of reactive dyes having amino-substituted naphthalenes as coupling components, of which the 2-aminonaphthalenesulfonic acids which are coupled in the 1-position especially are notable. The dyes of the general formula X

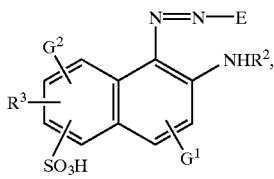

where

G¹ is hydrogen or hydroxysulfonyl,

G² is hydrogen or hydroxyl, and

E, R² and R³ are each as defined above, are therefore preferred above all.

Of the group of the reactive dyes of the formula X, emphasis is given to those in which R² and/or R³ are each hydrogen, C₁–C₄-alkyl which are substituted by hydroxysulfonyl or carboxyl, especially hydrogen, hydroxysulfonylmethyl or carboxymethyl.

Of the group of the dyes of the formula X, preference is given to those in which R² and/or R³ are each hydrogen, hydroxysulfonylmethyl or carboxymethyl, G¹ is hydrogen or hydroxysulfonyl, G² is hydrogen or hydroxyl and, in the radical E, L³ is a direct bond and A¹ is hydroxysulfonyl.

Particular preference is further given to the use of dyes of the formulae XIa and XIb

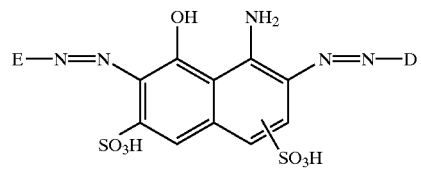

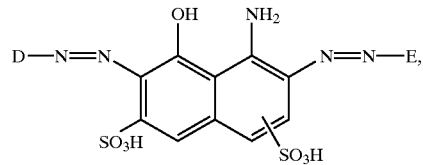

where the radical E is as defined above and D is the radical of a diazo component of the aniline or naphthalene series which optionally has further fiber-reactive groups, especially the group E, the group SO₂Y or those of the halotriazine series.

Preference for use is further given to the reactive dyes of the formula XII

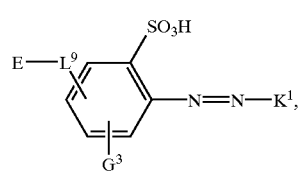

where

E and K¹ are each as defined above,

L⁹ is a radical of the formula O₂S—NZ¹, OC—NZ¹, Z¹N—SO₂, Z¹N—CO, Z¹N—CO—NZ², NZ¹ or

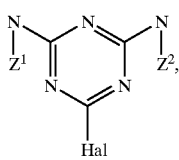

where $Z^1$, $Z^2$ and Hal are each as defined above, and $G^3$ is hydrogen, $C_1$–$C_4$-alkyl, $C_1$–$C_4$-alkoxy, chlorine or hydroxysulfonyl.

Preference for hair dyeing is further given to reactive dyes of the formula XIII

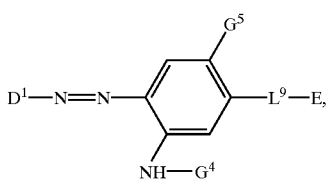

(XIII)

where
- $D^1$, E and $L^9$ are each as defined above,
- $G^4$ is $C_1$–$C_4$-alkanoyl, carbamoyl, mono- or di($C_1$–$C_4$) alkylcarbamoyl, phenylcarbamoyl or cyclohexylcarbamoyl, and
- $G^5$ is hydrogen, $C_1$–$C_4$-alkyl, $C_1$–$C_4$-alkoxy, hydroxysulfonyl or chlorine.

Preference is further given to using reactive dyes of the formulae XIVa and XIVb

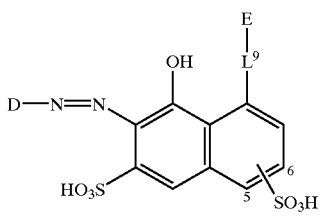

(XIVa)

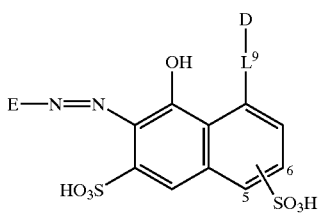

(XIVb)

where D, E and $L^9$ are each as defined above and the hydroxysulfonyl group is disposed in ring position 5 or 6.

Preference for use in hair dyeing is further given to reactive dyes of the formula XV

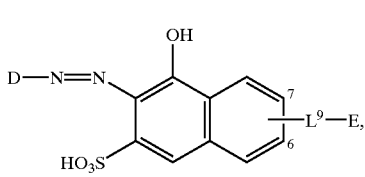

(XV)

where D, E and $L^9$ are each as defined above and the group —$L^9$—E is disposed in ring position 6 or 7.

Useful compounds further include those of the formula XVI

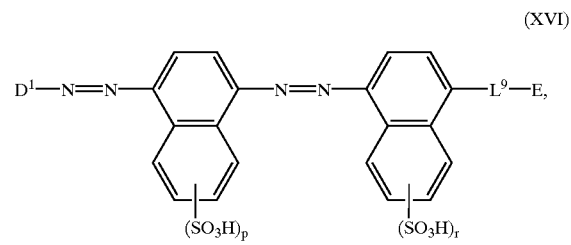

(XVI)

where $D^1$, E and $L^9$ are each as defined above and p and r are independently of each other 0, 1 or 2.

Useful compounds further include those of the formula XVII

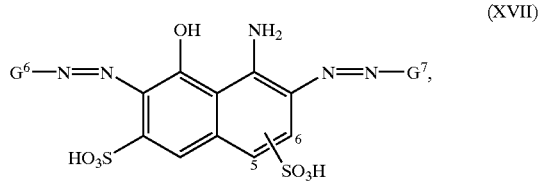

(XVII)

where one of the two radicals $G^6$ and $G^7$ is D, D having the abovementioned meaning, and the other is the radical

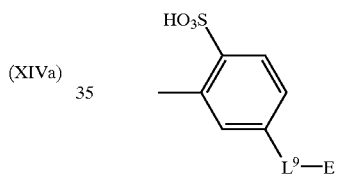

or else $G^6$ and $G^7$ are each a radical of the formula

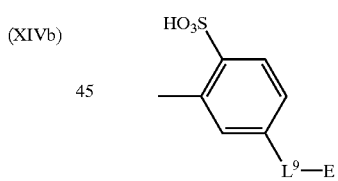

where $L^9$ and E are each as defined above.

Instead of the azo dye radicals, the dyes of the formula I may also contain corresponding metal complex azo dye radicals. Contemplated complexing metals include in particular copper, cobalt, chromium, nickel or iron, of which copper, cobalt or chromium are preferred.

The metallized groups are preferably disposed in each case ortho to the azo group, for example in the form of o,o'-dihydroxy-, o-hydroxy-o'-carboxy-, o-carboxy-o'-amino- or o-hydroxy-o'-amino-azo groups.

W in the formula I may also be for example the radical of a metallized formazan dye, in which case copper formazans should be mentioned in particular. Copper formazans are known per se and described for example in K. Venkataraman, The Chemistry of Synthetic Dyes, Vol. III, Academic Press, New York, London, 1970.

Particular preference is given to copper formazan dyes of the formula XIII

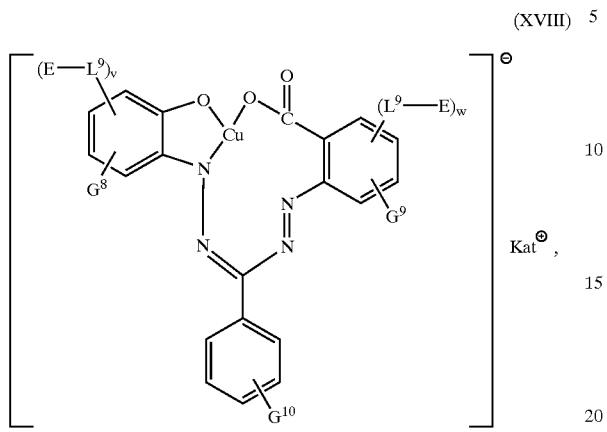

(XVIII)

where

Cat$^\oplus$ is the equivalent of a cation, $G^8_1$, $G^9$ and $G^{10}$ are identical or different and each is independently of the other hydrogen or hydroxysulfonyl, v is 0 or 1, w is 0 or 1, and E and $L^9$ are each as defined above, with the proviso that v and w are not both 0.

Kat$^\oplus$ in the formula XVIII is the equivalent of a cation. It is either a proton or derived from metal or ammonium ions. Metal ions are in particular the lithium, sodium or potassium ions. Ammonium ions for the purposes of this invention are the abovementioned substituted or unsubstituted ammonium cations.

Preferred cations are protons or lithium, sodium or potassium ions, the metal cations mentioned also being preferred cations when the reactive dyes XVIII are present in salt form.

One method of preparing the formazans underlying these dyes is described in EP-A-315 046 for example.

W in the formula I may also be for example the radical of an anthraquinone dye. Anthraquinones are known per se and described for example in K. Venkataraman, The Chemistry of Synthetic Dyes, Vol. II, Academic Press, New York, 1952.

Particular preference for dyeing hair is given to anthraquinone dyes of the formula XIX

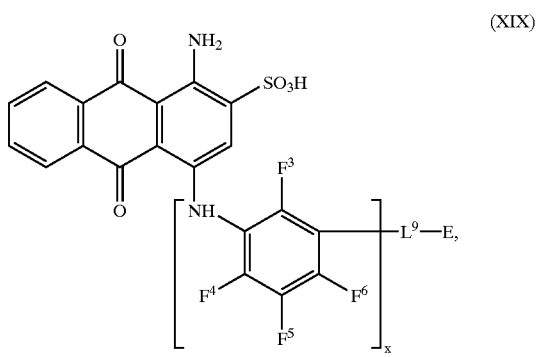

(XIX)

where

E and $L^9$ are each as defined above, x is 0 or 1

$F^3$ and $F^4$ are independently of each other hydrogen or methyl and one of the two radicals $F^5$ and $F^6$ is hydrogen or methyl and the other is hydroxysulfonyl.

W in the formula I may also be for example the radical of a triphendioxazine dye. Triphendioxazines are known per se and described for example in EP-A-141 359 or EP-A-311 969.

Suitable examples include triphendioxazine dyes of the formula XX

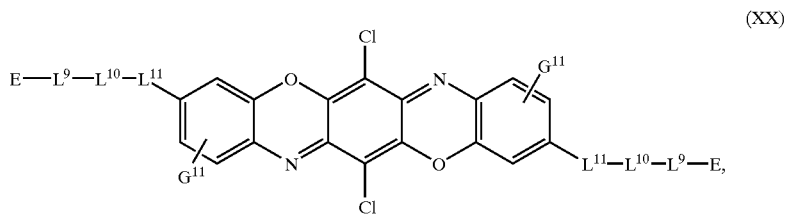

(XX)

where

E and $L^9$ are each as defined above, $G^{11}$ is hydroxysulfonyl or the radical $SO_2$—$C_2H_4$—$SO_3H$, $L^{10}$ is $C_2$–$C_4$-alkylene or phenylene, and $L^{11}$ is oxygen, imino or $C_1$–$C_4$-alkylimino.

W in the formula I may also be for example the radical of a metallized phthalocyanine dye. Phthalocyanines are known per se and described for example in F. H. Moser, D. L. Thomas, The Phthalocyanines, Vol. II, CRC Press, Boca Raton, Fla. 1983.

Particular preference is given to the phthalocyanine dyes of the formula XXI

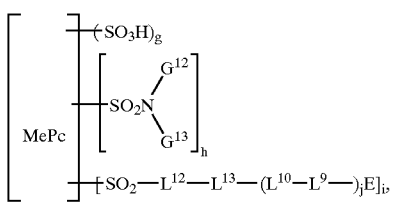
(XXI)

where
Pc is the phthalocyanine radical,
$G^{12}$ and $G^{13}$ are independently of each other hydrogen or $C_1$–$C_4$-alkyl,
$L^{12}$ is imino or $C_1$–$C_4$-alkylimino,
$L^{13}$ is a direct bond or $C_1$–$C_4$-alkylene,
Me is copper or nickel,
g is 0, 1 or 2,
h is 0, 1 or 2,
i is 1 or 2,
j is 0, 1, 2 or 3
and E, $L^9$ and $L^{10}$ are each as defined above.

Preference is further given to reactive dyes of the formula XXII

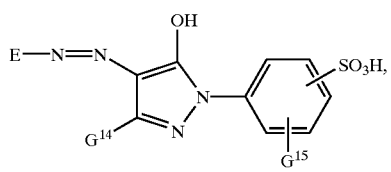
(XXII)

where
$G^{14}$ is methyl or carboxyl,
$G^{15}$ is hydrogen or hydroxysulfonyl,
and E is as defined above.

Preference is likewise given to reactive dyes of the formula XXIII

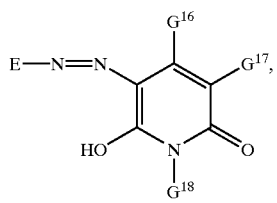
(XXIII)

where
$G^{16}$ is hydrogen or methyl,
$G^{17}$ is hydrogen, cyano, carbamoyl or hydroxysulfonylmethyl,
$G^{18}$ is methyl or ethyl,
and E is as defined above.

Since hair dyeing is generally not carried out with pure dyes, the use of mixtures of dyes of the formula I is expressly encompassed.

Furthermore, the reactive dyes of the formula I may be admixed with direct dyes such as azo dyes, anthraquinone dyes or nitro dyes of the benzene series to weaken or strengthen the colors produced.

The reactive dyes of the formula I can be prepared in a conventional manner.

When the radical W is linked to the fiber-reactive group E via a diazo bridge, the dyes of the invention are obtained by, for example, diazotizing and coupling the fiber-reactive compound of the formula XXIVa

where E is as defined above, in a conventional manner with a coupling component of the formula XXV

where $W^1$ is the radical of a coupling component, of a monoazo dye or additionally, when b=0, of a disazo dye, which may each have further reactive groups.

If, on the other hand, the radical W is linked to the fiber-reactive group E via one of the bridge members $L^9$ recited in case 2, the dyes of the invention can be prepared by reacting a suitable dye of the formula XXVI

where $W^2$ is the radical of a chromophore which optionally has further reactive groups and is derived from an optionally metallized mono- or disazo dye, a triphendioxazine, an anthraquinone, a metallized formazan or a metallized phthalocyanine and $G^{14}$ is an amino radical of the formula $NHZ^1$ or an acid halide radical of the formula COHal or $SO_2$Hal, where $Z^1$ and Hal are each as defined above, with a fiber-reactive compound of the formula XXVIb

where E is as defined above and $G^{20}$ is one of the radicals $G^{19}$, with the proviso that, in either case, an amine reacts with an acid halide.

When $L^9$ (case 2) is a urea bridge or a triazine radical, the synthesis steps customary with these classes of compounds are included as well.

It is also possible to start from such precursors of compounds of the formula XXVI as form part of the later chromophore and to react them first with the fiber-reactive compound XXVIb and then to construct the chromophore radical $W^2$.

When b in the formula I is 1, the bridged chromophores can be obtained for example by either bridging the finished individual chromophores or else by first bridging suitable intermediates and then constructing the respective chromophoric systems.

Furthermore, U.S. Pat. No. 4,066,638, EP-A-107 614, EP-A-107617, EP-A-559 617, EP-A-581 729, EP-A-693 536, DE-A-3441272, DE-A-3441273, DE-A-4437265, EP-A-637615, EP-A-318968, JP-A-7118830, JP-A-7128904, NL-A-7410432, EP-A-637615, DE-A-19600765, DE-A-4434989, DE-A-19523245 DE-A-2 154 942 and prior German publication DE-A 19611667, for example, describe dyes which fall within the general formula I.

The use in hair dyeing of the dyes recited as examples in these documents is expressly encompassed.

The present invention further provides cosmetic preparations comprising the above dyes as well as customary hair dyeing assistants.

The dyes are used in dissolved form in an aqueous cosmetically acceptable medium. In the aqueous cosmetically acceptable carrier, the pH varies within the range from 5 to 9 and is preferably 6–8. It is adjusted to the desired value with the aid of mild inorganic or organic bases, salts, weak acids or buffers. Examples are ammonia, ammonium carbonate, potassium carbonate, sodium carbonate, sodium hydroxide such as mono-, di- or triethanolamine, disodium hydrogenphosphate, sodium citrate or sodium borate.

The dyes are present in the hair colorants in proportions from 0.01 to 10% by weight, based on the total weight of the preparation.

Customary assistants in cosmetic preparations for hair dyeing are anionic, cationic, nonionic or amphoteric surfactants or mixtures thereof. Suitable surfactants are soaps, alkylbenzenesulfonates, alkylnaphthalenesulfonates, sulfates, ether sulfates and sulfonates of fatty alcohols, quaternary ammonium salts, such as trimethylcetylammonium bromide, cetylpyridinium bromide, quaternium 1 to X (INCI), cocoyltrimethylammonium methylsulfate (INCI), hydroxyethylcetyldimomium phosphate (INCI), cetyltrimethylammonium chloride, optionally ethoxylated fatty acid ethanolamides, polyethoxylated acids, alcohols or amines, polyglycerated alcohols, polyethoxylated or polyglycerated alkylphenols and also polyethoxylated alkyl sulfates. Surfactants are present in the compositions of the invention in an amount from 0.5 to 40% by weight, based on the total weight of the preparation.

Further customary assistants are organic solvents such as solubilizers, eg. $C_1$–$C_4$-alcohol such as ethanol and isopropanol, glycols, glycol ethers such as ethylene glycol, propylene glycol, 2-methoxyethanol, 2-ethoxyethanol or 2-butoxyethanol, and also glycerol. Solvents are generally present in an amount of 0–40% by weight, based on the total weight of the preparation.

To simplify the handling of the preparation, it is customary to add thickeners to the preparations of the invention as assistants. Customary thickeners are cellulose derivatives such as methyl-, hydroxymethyl-, hydroxyethyl-, hydroxypropyl- or carboxymethyl-cellulose, sodium alginate, gum arabic, xanthan gum, tragacanth, acrylic acid polymers, polyvinylpyrrolidone, vinyl acetate/crotonic acid copolymers, vinyl acetate/vinylpyrrolidone copolymers, butyl vinyl ether/maleic anhydride copolymers, methyl vinyl ether/maleic anhydride copolymers, or an inorganic thickener such as bentonite. These thickeners are generally used in an amount of up to 5% by weight based on the total weight of the preparation.

Hair-cosmetic preparations which are to be used in the form of gels further comprise gel-forming substances such as, for example, carbomers (INCI). For certain caring properties, the preparations may further comprise cationic poymers and silicone compounds. Suitable cationic polymers are, for example, polyquaternium 1 to x as per INCI, copolymers of vinylpyrrolidone/vinylimidazolium salts (Luviquat® FC, Luviquat HM, manufacturer: BASF), copolymers of vinylpyrrolidone/dimethylaminoethyl methacrylate, quaternized with diethyl sulfate (Luviquat PQ 11); cationic cellulose derivatives (Polyquaternium-4 and 10), acrylamido copolymers (Polyquaternium-7) and cationic guar gum derivatives, eg. guar hydroxypropyltriminium chloride (INCI). Suitable silicone compounds are, for example, polyalkylsiloxanes, polyarylsiloxanes, polyarylalkylsiloxanes, polyethersiloxanes or silicone resins.

Further customary assistants are mild antioxidants which do not react with the dyes, penetrants, sequestrants, buffers, perfume oil, sunscreens (UV-A and UV-B), preservatives, hair-cleaning products and biologically active substances such as pantheonol, bisabolol and vitamins, for example of type A, C and E.

The cosmetic preparations of the invention can be used for dyeing hair in liquid form, generally thickened, as cream, paste, as gel or in some other suitable form.

In a preferred application, the preparation is applied to the hair, allowed to act on the hair for from 5 to 50 minutes, preferably from 10 to 30 minutes, and then the hair is rinsed and, if necessary, washed with a conventional shampoo.

A warm preparation or external heat can be used to speed up the dyeing or deepen the dyeing over the same treatment time. Preference is given to using temperatures within the range from 20 to 40° C.

The reactive dyes of the formula I produce uniform dyeings and good coverage of white hair. The dyeings are lightfast, washfast, weatherfast and rubfast.

Furthermore, reactive dyes and their alternative dyeing method make it possible to dispense with $H_2O_2$ as an oxidant in the dyeing process. What is particularly advantageous here is the fact that the hue is predetermined by the dye and not developed on the hair. This simplifies the preparation of dye mixtures and shading.

They are furthermore known to be physiologically safe from their use as textile dyes.

The Examples which follow illustrate the invention.

EXAMPLE 1

1.25 g of the reactive dye of the formula 1

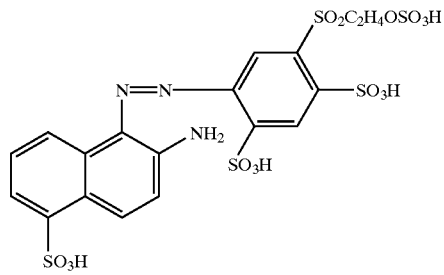

were dissolved in 25 ml of water and the solution was adjusted to pH 7 with sodium hydrogenphosphate. After the solution was heated to 36° C., a bleached strand of human hair (2 g) was immersed into the solution for 20 minutes. Thereafter the hair was rinsed with water and air dried. A deep reddish scarlet hair dyeing ($\lambda$ max=508 nm, reflectance) was obtained.

Dyeings were obtained under similar conditions with the dyes recited in the examples which follow, where $E^1$ and $E^2$ are the radicals of the formulae

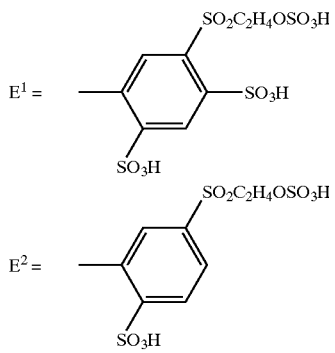

respectively.

EXAMPLE 2

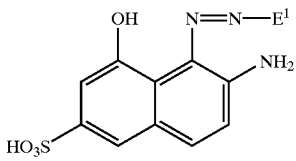

NH$_2$ (described in Ex. 4 of U.S. Pat. No. 4,066,638) bluish red ($\lambda$ max=534, reflectance)

EXAMPLE 3

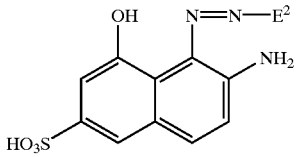

(described in Ex. 1 of DE-A 214942) bluish red ($\lambda$ max=539, reflectance)

EXAMPLE 4

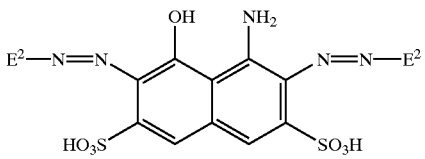

(described in Ex. 1 of DE-A-19523245) dark blue

EXAMPLE 5

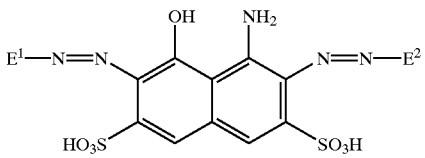

(prepared similarly to Ex. 1 of DE-A-19523245) dark blue

EXAMPLE 6

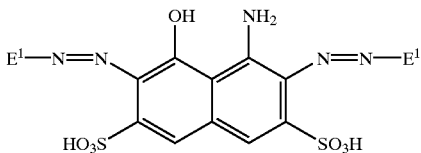

(prepared similarly to Ex. 1 of DE-A-19523245) dark blue

EXAMPLE 7

(similarly to Ex. 79 of U.S. Pat. No. 4,066,638) yellowish brown

Preparation method relating to Example 1

131 g of 1-amino-3-($\beta$-sulfatoethylsulfonyl)benzene-4,6-disulfonic acid were suspended in 700 ml of ice-water and 60 ml of hydrochloric acid (30% strength by weight) and admixed at 0–5° C. with 60 ml of 23% strength by weight sodium nitrite solution added a little at a time. After diazotization had ended, the small excess of nitrite was destroyed with some amidosulfuric acid. 60 g of 2-aminonaphthalene-5-sulfonic acid in 800 ml of ice-water were added to this reaction mixture at 0–5° C., a pH of 2–3 was maintained with sodium acetate, and the batch was gradually warmed to 20° C. Once diazo compound was no longer detectable, the pH was adjusted to 5 with sodium bicarbonate, and the batch was clarified by filtration. The dye was precipitated by addition of 500 g of sodium chloride, filtered off with suction and dried at 40° C. under reduced pressure, leaving a readily water-soluble reddish powder. A similar dye is described in Example 3 of U.S. Pat. No. 406,638.

The dyes in Examples 2, 3 and 7 were prepared in a similar manner.

Formulation Examples

A) Hair-dyeing Cream
Phase I
  1.5 g of ceteareth-6 (and) stearyl alcohol (INCI)
  1.5 g of ceteareth-25
  6.0 g of cetearyl octanoate
  3.0 g of cetearyl alcohol
Phase II
  2 g of reactive dye of the formula 1
  2 g of propylene glycol
  84 g of dist. water
  q.s. citric acid/triethanolamine to adjust to pH 7
  q.s. preservative
Phase III
  q.s. perfume oil The ingredients were dissolved at 60° C., and then Phase I was added to Phase II. Phase III was added after cooling to 30° C.

A bleached strand of human hair (2 g) was treated with 0.5 g of the dyeing cream and left for 20 min. It was then rinsed with water, leaving a hair dyeing as described in Example 1.

B) Hair-dyeing Lotion
  5 g of reactive dye of the formula 1
  1.2 g of Natrosol 250 HR (manufacturer: Aqualon), (hydroxyethylcellulose to INCI)
  1 g of propylene glycol
  ad 100 g of dist. water
  q.s. preservative A bleached strand of human hair (2 g) was treated with 0.5 g of the dyeing lotion and left for 20 min. It was then rinsed with water, leaving a hair dyeing as described in Example 1.

C) Hair-dyeing Mousse 2 g of reactive dye of the formula 1

3 g of Luviskol® VA 64 (manufacturer: BASF), (PVP/VA copolymer to INCI)

0.45 g of ceteareth-25 (INCI)

0.10 g of dimethicone (INCI)

10 g of propane/butane ad 100 g of dist. water q.s. preservative

A bleached strand of human hair (2 g) was treated with 0.5 g of the hair-dyeing mousse, left for 15 min and then rinsed with water. As well as being deeply colored, the hair was very easy to comb through and looked cared-for. The hair dyeing obtained was as described in Example 1.

D) Hair-dyeing Shampoo 5 g of reactive dye of the formula 1

40 g of sodium laurylethersulfate to INCI (Texapon® N 28, manufacturer: Henkel)

10 g of Tego® Betain L 7 (manufacturer: Goldschmidt) (cocamidopropyl betaine to INCI)

2 g of Gluatin WQ (wheat germ protein)

ad 100 g of dist. water q.s. preservative q.s. sodium chloride as thickener

The use of a hair-dyeing shampoo makes it possible to combine cleaning and dyeing of the hair. A bleached strand of human hair (2 g) was treated with 0.5 g of the hair-dyeing shampoo and rinsed out after 1 min to the disappearance of foam. The hair dyeing obtained was as described in Example 1.

E) Dyeing Paste 2 g of reactive dye of formula 1

7 g of titanium dioxide 15 g of aerosil® (manufacturer: Degussa)

10 g of Lutrol® F 127 (polyethylene glycol, manufacturer: BASF)

ad 100 g of dist. water q.s. preservative

A bleached strand of human hair (2 g) was treated with 0.5 g of the hair-dyeing paste, left for 15 min and then rinsed with water. The hair dyeing obtained was as described in Example 1.

F) Hair-dyeing Shampoo 10 g of reactive dye of formula 1

2.20 g of xanthan gum (Keltrol® T, manufacturer: Kelco)

20.0 g of sodium laurylethersulfate 2.50 g of olein diethanolamide 0.10 g of Trilon® B (manufacturer: BASF)

ad 100 g of dist. water 45 q.s. preservative 25 g of the dyeing paste were suspended with 25 ml of dist. water, a bleached strand of human hair (2 g) was treated with this dyeing shampoo and left for 20 min. It was then rinsed out with water. The hair dyeing obtained was as described in Example 1.

What is claimed is:

1. A method of dyeing human hair, comprising applying to the hair a reactive dye of the formula I:

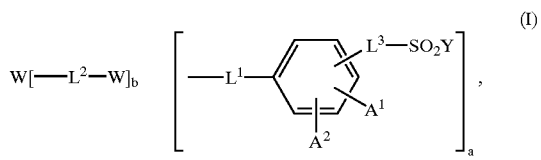

wherein a is 1 or 2, b is 0 or 1,

Y is vinyl or a radical of the formula $C_2H_4Q$, where Q is an alkali-detachable group, $L^3$ is a direct bond or a bridge member of the formula CO—NH—$M^1$, where $M^1$ is $C_2$–$C_6$-alkylene with or without interruption by 1 or 2 unadjacent oxygen atoms, imino or $C_1$–$C_4$-alkylimino groups, $A^1$ is hydroxysulfonyl or a radical of the formula $SO_2Y$, $A^2$ is hydrogen, hydroxysulfonyl, methoxy, chlorine, bromine or carboxyl, W is either in case 1) the radical of a coupling component, of a monoazo dye or additionally, when b=0, of a disazo dye, which may each bear further fiber-reactive groups, or in case 2) the radical of a chromophore which optionally has further fiber-reactive groups and is derived from an optionally metallized mono- or disazo dye, from a triphendioxazine, from an anthraquinone, from a metallized formazan or from a metallized phthalocyanine, $L^1$ is either in case 1) an azo bridge or in case 2) a bridge member of the formula $O_2S$—$NZ^1$, OC—$NZ^1$, $Z^1N$—$SO_2$, $Z^1N$—CO, $Z^1N$—CO—$NZ^2$, $NZ^1$ or

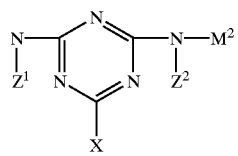

where $M^2$ is a direct bond or methylene, $Z^1$ and $Z^2$ are each independently of the other hydrogen, $C_1$–$C_6$-alkyl or phenyl and X is fluorine, chlorine or bromine, amino, $C_1$–$C_6$-alkylamino with or without interruption by 1 or 2 unadjacent oxygen atoms, imino or $C_1$–$C_4$-alkylimino groups and with or without hydroxyl substitution, N-pyrrolidinyl, N-piperidinyl, N-morpholinyl, N-piperazinyl or N-($C_1$–$C_4$)-alkylpiperazinyl, or $NZ^1$ or $NZ^2$ each also represent 1,4-piperazinediyl, $L^2$ is a radical of the formula

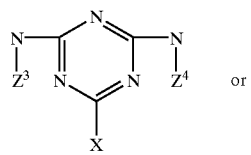 or

-continued

[Structure: triazine-N-L⁴-N-triazine with Z³, Z⁴, Z⁵, Z⁶ substituents and X groups]

where $Z^3$, $Z^4$, $Z^5$ and $Z^6$ are each independently of the others hydrogen, $C_1$–$C_6$-alkyl or phenyl, $L^4$ is $C_2$–$C_8$-alkylene or unsubstituted or $C_1$–$C_4$-alkyl-, $C_1$–$C_4$-alkoxy- or hydroxysulfonyl-substituted phenylene, and X is in each case as defined above.

2. The method of claim 1, wherein $L^3$ is a direct bond.

3. The method of claim 1, wherein $A^1$ is hydroxysulfonyl.

4. The method of claim 1, wherein $A^2$ is hydrogen or hydroxysulfonyl.

5. The method of claim 1, wherein $L^1$ is an azo bridge.

6. The method of claim 1, wherein $L^1$ is a bridge member of the formula

[Structure: triazine with two NH groups and X]

in case 2).

7. The method of claim 1, wherefor Y is vinyl or a radical of the formula $C_2H_4OSO_3H$.

8. A cosmetic composition, comprising at least one hair dyeing assistant and one or more dyes of the formula I:

$$W[-L^2-W]_b \quad \left[ -L^1-\underset{A^2}{\overset{L^3-SO_2Y}{\diagup\!\!\!\diagdown\!\!A^1}} \right]_a \quad (I)$$

wherein a is 1 or 2, b is 0 or 1,

Y is vinyl or a radical of the formula $C_2H_4Q$, where Q is an alkali-detachable group, $L^3$ is a direct bond or a bridge member of the formula CO—NH—$M^1$, where $M^1$ is $C_2$–$C_6$-alkylene with or without interruption by 1 or 2 unadjacent oxygen atoms, imino or $C_1$–$C_4$-alkylimino groups, $A^1$ is hydroxysulfonyl or a radical of the formula $SO_2Y$, $A^2$ is hydrogen, hydroxysulfonyl, methoxy, chlorine, bromine or carboxyl, W is either in case 1) the radical of a coupling component, of a monoazo dye or additionally, when b=0, of a disazo dye, which may each bear further fiber-reactive groups, or in case 2) the radical of a chromophore which optionally has further fiber-reactive groups and is derived from an optionally metallized mono- or disazo dye, from a triphendioxazine, from an anthraquinone, from a metallized formazan or from a metallized phthalocyanine, $L^1$ is either in case 1) an azo bridge or in case 2) a bridge member of the formula $O_2S$—$NZ^1$, OC—$NZ^1$, $Z^1N$—$SO_2$, $Z^1N$—CO, $Z^1N$—CO—$NZ^2$, $NZ^1$ or

[Structure: triazine with N—$M^2$ substituent, $Z^1$, $Z^2$ and X]

where $M^2$ is a direct bond or methylene, $Z^1$ and $Z^2$ are each independently of the other hydrogen, $C_1$–$C_6$-alkyl or phenyl and X is fluorine, chlorine or bromine, amino, $C_1$–$C_6$-alkylamino with or without interruption by 1 or 2 unadjacent oxygen atoms, imino or $C_1$–$C_4$-alkylimino groups and with or without hydroxyl substitution, N-pyrrolidinyl, N-piperidinyl, N-morpholinyl, N-piperazinyl or N-($C_1$–$C_4$)-alkylpiperazinyl, or $NZ^1$ or $NZ^2$ each also represent 1,4-piperazinediyl, $L^2$ is a radical of the formula

[Structure: triazine with $Z^3$, $Z^4$ and X]  or

[Structure: bis-triazine bridged by N-L⁴-N with $Z^3$, $Z^4$, $Z^5$, $Z^6$ and X groups]

where $Z^3$, $Z^4$, $Z^5$ and $Z^6$ are each independently of the others hydrogen, $C_1$–$C_6$-alkyl or phenyl, $L^4$ is $C_2$–$C_8$-alkylene or unsubstituted or $C_1$–$C_4$-alkyl-, $C_1$–$C_4$-alkoxy- or hydroxysulfonyl-substituted phenylene, and X is in each case as defined above.

9. The cosmetic composition of claim 8, wherein $L^3$ is a direct bond.

10. The cosmetic composition of claim 8, wherein $A^1$ is hydroxysulfonyl.

11. The cosmetic composition of claim 8, wherein $A^2$ is hydrogen or hydroxysulfonyl.

12. The cosmetic composition of claim 8, wherein $L^1$ is an azo bridge.

13. The cosmetic composition of claim 8, wherein $L^1$ is a bridge member of the formula

[Structure: triazine with two NH groups and X]

in case 2).

14. The cosmetic composition of claim 8, wherein Y is vinyl or a radical of the formula $C_2H_4OSO_3H$.

15. The cosmetic composition of claim 8, further comprising an aqueous cosmetically acceptable medium, wherein the dye is dissolved in the aqueous cosmetically acceptable medium.

16. The cosmetic composition of claim 15, having a pH of 5 to 9.

17. The cosmetic composition of claim 8, wherein the dye is present in an amount of from 0.01 to 10% by weight, based on the total weight of the composition.

18. The cosmetic composition of claim 8, wherein the assistant comprises at least one surfactant selected from the group consisting of anionic, cationic, nonionic, amphoteric surfactant, and a mixture thereof.

19. The cosmetic composition of claim 18, wherein the surfactant is present in the composition in an amount of 0.5 to 40% by weight, based on the total weight of the composition.

20. The cosmetic composition of claim 8, wherein the assistant comprises at least one selected from the group consisting of soaps, alkylbenzenesulfonates, alkylnaphthalenesulfonates, sulfates, ether sulfates of fatty alcohols, ether sulfonates of fatty alcohols, quaternary ammonium salts, trimethylcetylammonium bromide, cetylpyridinium bromide, quaternium 1 to X, cocoyltrimethylammonium methylsulfate, hydroxyethylcetyldimomium phosphate, cetyltrimethylammonium chloride, optionally ethoxylated fatty acid ethanolamides, polyethoxylated acids, polyethoxylated alcohols, polyethoxylated amines, polyglycerated alcohols, polyethoxylated alkylphenols polyglycerated alkylphenols, and polyethoxylated alkyl sulfates.

21. The cosmetic composition of claim 8, wherein the assistant comprises at least one organic solvent selected from the group consisting of $C_1$–$C_4$-alcohol, ethanol, isopropanol, glycols, glycol ethers, ethylene glycol, propylene glycol, 2-methoxyethanol, 2-ethoxyethanol, 2-butoxyethanol and glycerol.

22. The cosmetic composition of claim 21, wherein the solvent is present in an amount of 0–40% by weight, based on the total weight of the composition.

23. The cosmetic composition of claim 8, further comprising at least one thickener selected from the group consisting of cellulose derivatives, methyl-cellulose, hydroxymethyl-cellulose, hydroxyethyl-cellulose, hydroxypropyl-cellulose, carboxymethyl-cellulose, sodium alginate, gum arabic, xanthan gum, tragacanth, acrylic acid polymers, polyvinylpyrrolidone, vinyl acetate/crotonic acid copolymers, vinyl acetate/vinylpyrrolidone copolymers, butyl vinyl ether/malefic anhydride copolymers, methyl vinyl ether/malefic anhydride copolymers, inorganic thickener, and bentonite.

24. The cosmetic composition of claim 23, wherein the thickener is present in an amount of up to 5% by weight, based on the total weight of the composition.

25. The cosmetic composition of claim 8, further comprising at least one substance selected from the group consisting of carbomers, cationic polymers, silicone compounds, polyquaternium 1 to x, copolymers of vinylpyrrolidone/vinylimidazolium salts, copolymers of vinylpyrrolidone/dimethylaminoethyl methacrylate quaternized with diethyl sulfate, cationic cellulose derivatives, acrylamido copolymers, cationic guar gum derivatives, guar hydroxypropyltriminium chloride, polyalkylsiloxanes, polyarylsiloxanes, polyarylalkylsiloxanes, polyethersiloxanes and silicone resins.

\* \* \* \* \*